US011803781B2

(12) United States Patent
Foster et al.

(10) Patent No.: US 11,803,781 B2
(45) Date of Patent: Oct. 31, 2023

(54) MACHINE LEARNING FOR NUTRIENT QUANTITY ESTIMATION IN SCORE-BASED DIETS AND METHODS OF USE THEREOF

(71) Applicant: WW International, Inc., New York, NY (US)

(72) Inventors: Gary Foster, Newtown Square, PA (US); Ute Gerwig, Duesseldorf (DE); Laura Smith, Bridgeport, CT (US); Reka Daniel-Weiner, New York, NY (US); Michael Skarlinski, New York, NY (US); Judith Bünker, Dulmen (DE); Jacquelyn Zaydel, Jersey City, NJ (US)

(73) Assignee: Weight Watchers International, Inc., New York, NY (US)

( * ) Notice: Subject to any disclaimer, the term of this patent is extended or adjusted under 35 U.S.C. 154(b) by 0 days.

(21) Appl. No.: 17/940,798

(22) Filed: Sep. 8, 2022

(65) Prior Publication Data

US 2023/0079862 A1    Mar. 16, 2023

Related U.S. Application Data

(60) Provisional application No. 63/241,894, filed on Sep. 8, 2021.

(51) Int. Cl.
*G06N 20/20*    (2019.01)
(52) U.S. Cl.
CPC .................................. *G06N 20/20* (2019.01)
(58) Field of Classification Search
CPC ...................................................... G06N 20/20
(Continued)

(56) References Cited

U.S. PATENT DOCUMENTS

2018/0089585 A1\*  3/2018  Rickard, Jr. ............ G06N 20/00
2019/0189242 A1\*  6/2019  Angiuoli ................ G16B 40/20
(Continued)

FOREIGN PATENT DOCUMENTS

KR    20180086602 A    8/2018

OTHER PUBLICATIONS

Ramoelo, et al., Monitoring grass nutrients and biomass as indicators of rangeland quality and quantity using random forest modelling and WorldView-2 data, International Journal of Applied Earth Observation and Geoinformation 43 (2015) 43-54 (Year: 2015).\*

(Continued)

*Primary Examiner* — Tsu-Chang Lee
(74) *Attorney, Agent, or Firm* — Greenberg Traurig, LLP

(57) ABSTRACT

Systems and methods of the present disclosure use one or more processor(s) to receive a consumable preference and a daily score intake value associated with a user and to obtain a content data regarding consumable item including an amount of a first nutrient found in the consumable item. The processor(s) utilizes, in real-time, a nutrient prediction machine learning model to ingest the content data regarding the consumable item and predict an amount of a second nutrient in the consumable item based on the content data and a decision tree library of thousand nutrient decision trees. The processor(s) determines zero-scored consumable item based on the daily score intake value, the amount of the first nutrient, the amount of the second nutrient, and the consumable preference. The processor(s) instructs a computing device to utilize a graphical user interface element to identify the zero-scored consumable item on a screen of the computing device.

16 Claims, 15 Drawing Sheets

(58) Field of Classification Search
USPC .......................................................... 706/12
See application file for complete search history.

(56) References Cited

U.S. PATENT DOCUMENTS

2020/0227156 A1  7/2020  Mainardi et al.
2020/0321122 A1  10/2020  Neumann

OTHER PUBLICATIONS

International Search Report and Written Opinion from International Appln. No. PCT/US22/42930 dated Dec. 13, 2022.

* cited by examiner

MACHINE LEARNING FOR NUTRIENT QUANTITY ESTIMATION IN SCORE-BASED DIETS AND METHODS OF USE THEREOF

CROSS-REFERENCE TO RELATED APPLICATIONS

The present application claims priority to U.S. Provisional Application No. 63/241,894 filed on 8 Sep. 2021, which is incorporated herein by reference in its entirety.

FIELD OF TECHNOLOGY

The present disclosure generally relates to computer-based platforms/systems configured for machine learning for nutrient quantity estimation in score-based diets and methods of use thereof, including machine-learning based prediction of sugar and/or added sugar quantities.

BACKGROUND OF TECHNOLOGY

The prevalence of diabetes and obesity has consistently trended upward across the globe. As the number of people with diabetes has hit an almost four-fold increase since 1980 and the number of people with obesity nearly tripled since 1975, these two chronic conditions have emerged as imminent threats to public health. Although genetic factors contribute significantly to both diabetes and obesity, one's environment and lifestyle can have an influence as well. Nutrition and diet can be included as both environmental and lifestyle factors, reflecting components such as obesogenic environments within community settings, which influences individual food selection and eating behaviors. As such, nutrition and diet elicit a complex role within the multifactorial network of potential mechanisms contributing to obesity and diabetes.

Ultra-processed food and more specifically, the added sugar within, is considered to be a key contributor toward poor nutrition and diet that can lead to development of both obesity and diabetes. The 2020 Dietary Guidelines for Americans recommend that added sugar intake be limited to 10 percent of daily calories consumed, yet the average added sugar consumption per day is greater than 13 percent and most commonly comes from sugar-sweetened beverages. Additional common sources of added sugar include desserts and sweet snacks, coffee and tea, candy, breakfast cereals and bars, sandwiches, and higher fat milk and yogurt. Between 2000 and 2013, the number of available products with added sweeteners, particularly beverages, significantly increased. Rapid changes in the food supply also indicated that while consumption of food and beverages with caloric sweeteners slowly declined, a new trend demonstrating the purchase of products with low-calorie sweeteners combined with caloric sweeteners had begun. In response, the U.S. Food and Drug Administration amended the Nutrition Facts label in 2016 to include information about added sugars and required that all labels present this information to consumers by Jan. 1, 2021. This represented the first update to the Nutrition Facts label in over 20 years.

Many other countries across the world (i.e., Chile, Australia, New Zealand) and the European Union have started labeling sugar information on packaged products, however, to date only the U.S. differentiates to include added sugar in addition to total sugar on the Nutrition Facts label. The lack of access to information about added sugars in most parts of the world can create difficulty among consumers attempting to make an informed decision regarding which products to purchase and/or consume. Even when labeled sugar information is present, complexity in format and insufficient understanding of dietary sugar recommendations often further complicate the message. A recent review focused on the effectiveness of various sugar labels found that format can be highly influential. Reporting sugar content in grams along with illustrations and direct statements was determined to be more effective than a standalone Nutrition Facts label.

These previous findings indicate that broad access to in-depth nutrition information, especially regarding sugar and added sugar content, has the potential to positively influence overall obesity and diabetes rates in a population. While releasing legislation mandating disclosure of such nutrition statements directly on the packaging of food products is a time-consuming process, and added sugar is currently not required to be disclosed in most countries, a growing proportion of the world's population has access to the digital devices, which opens up the potential for digital solutions that support health decisions.

The same may be said of other nutrients. Calories, fiber, protein, fat, unsaturated fat, saturated fat, trans fat and other nutrients are expressed in different formats and different levels of detail across the world. Thus, reliably determining the amounts of each nutrient in a food product, beverage, or other consumable is an obstacle to effective diet and weight management.

SUMMARY OF DESCRIBED SUBJECT MATTER

Recent advances in data science have made it possible to build gradient boosted tree models that exploit subtle non-linear interactions between predictors, and use these models in production environments to serve results to users at scale, either through a website or a smartphone app.

In some embodiments, such advances may be leveraged to train a gradient boosted tree model to predict the amounts of one or more nutrients in a consumable, such as the added sugar content of foods. In some embodiments, such a prediction may enable clinically important nutrition predictions that can inform consumer behavior.

In some embodiments, the present disclosure provides various exemplary technically improved computer-implemented systems, e.g., a system configured to perform a method having steps such as: receiving, by a processor, from a computing device associated with a user, at least one consumable preference associated with the user; where the at least one consumable preference identifies the at least one food category, the at least one beverage category or a combination thereof; receiving, by the processor, a daily score intake value associated with the user; obtaining, by the processor, a content data regarding at least one consumable item; where the at least one consumable item is at least one food item, at least one beverage item, or a combination thereof; where the content data includes a first content data item identifying at least one first amount of at least one first nutrient found in the at least one consumable item; where the consumable-specific machine learning model includes a subset of decision trees selected from the decision tree library; where the automatically generating the consumable-specific machine learning model further includes: determining a plurality of optimal places to generate tree branches for a subset of decision trees selected from the decision tree library; automatically applying, by the processor, in real-time, a nutrient prediction machine learning model to the content data regarding the at least one consumable item to predict the at least one second amount of the at least one second nutrient in the at least one consumable item based at least in part on: i) the first content data item identifying the at least one first amount of the at least one first nutrient found in the at least one consumable item, and iii) a decision tree library of at least one thousand nutrient decision trees; determining, by the processor, at least one zero-scored consumable item based, at least in part, on: i) the daily score intake value associated with the user, ii) the at least one first amount of the at least one first nutrient, iii) the at least one second amount of the at least one second nutrient, and iv) the at least one consumable preference; and instructing, by the processor, the computing device associated with the user to utilize at least one graphical user interface element to identify the at least one zero-scored consumable item on a screen of the computing device.

In some aspects, the techniques described herein relate to a computer-based method including: receiving, by a processor, from a computing device associated with a user, at least one consumable preference associated with the user; wherein the at least one consumable preference identifies the at least one food category, the at least one beverage category or a combination thereof; receiving, by the processor, a daily score intake value associated with the user; obtaining, by the processor, a content data regarding at least one consumable item; wherein the at least one consumable item is at least one food item, at least one beverage item, or a combination thereof; wherein the content data includes a first content data item identifying at least one first amount of at least one first nutrient found in the at least one consumable item; automatically applying, by the processor, in real-time, a nutrient prediction machine learning model to the content data regarding the at least one consumable item to predict at least one second amount of at least one second nutrient in the at least one consumable item based at least in part on: i) the first content data item identifying the at least one first amount of the at least one first nutrient found in the at least one consumable item, and ii) a decision tree library of at least one thousand nutrient decision trees; determining, by the processor, at least one zero-scored consumable item based, at least in part, on: i) the daily score intake value associated with the user, ii) the at least one first amount of the at least one first nutrient, iii) the at least one second amount of the at least one second nutrient, and iv) the at least one consumable preference; and instructing, by the processor, the computing device associated with the user to utilize at least one graphical user interface element to identify the at least one zero-scored consumable item on a screen of the computing device.

In some aspects, the techniques described herein relate to a method, wherein the nutrient prediction machine learning model includes a decision tree model having a subset of decision trees from the decision tree library; wherein each decision tree of the subset of decision trees includes a plurality of branches and a plurality of leaves; and wherein the decision tree model is trained to form each branch of the plurality of branches based at least in part on learned threshold values of nutrient quantities.

In some aspects, the techniques described herein relate to a method, further including: selecting, by the at least one processor, the subset of decision trees from the decision tree library based at least in part on the content data; applying, by the at least one processor, each decision tree in the subset of decision trees to the content data to predict the at least one decision tree-specific second amount of the at least one second nutrient in the at least one consumable item based at least in part on: i) the first content data item identifying the at least one first amount of the at least one first nutrient found in the at least one consumable item, and ii) a second content data item identifying the at least one second nutrient having the at least one decision tree-specific second amount found in the at least one consumable item; and aggregating, by the at least one processor, the at least one decision tree-specific second amount of each decision tree to produce the at least one second amount.

In some aspects, the techniques described herein relate to a method, further including: receiving, by the at least one processor, at least one known second amount representative of at least one actual amount of the at least one second nutrient in the at least one consumable item; determining, by the at least one processor, at least one second nutrient prediction error based at least in part on a different between the at least one second amount and the at least one known second amount; and updating, by the at least one processor, the learned threshold values of nutrient quantities of each branch of the plurality of branches of each decision tree in the subset of decision trees based at least in part on the at least one second nutrient prediction error.

In some aspects, the techniques described herein relate to a method, further including pruning, by the at least one processor, the subset of decision trees based at least in part on the at least one second nutrient prediction error.

In some aspects, the techniques described herein relate to a method, further including: selecting, by the at least one processor, the subset of decision trees from the decision tree library based at least in part on model parameters; receiving, by the at least one processor, at least one known second amount representative of at least one actual amount of the at least one second nutrient in the at least one consumable item; determining, by the at least one processor, at least one second nutrient prediction error based at least in part on a different between the at least one second amount and the at least one known second amount; and updating, by the at least one processor, the model parameters based at least in part on the at least one second nutrient prediction error.

In some aspects, the techniques described herein relate to a method, wherein the nutrient prediction machine learning model includes a random forest.

In some aspects, the techniques described herein relate to a method, further including: instructing, by the processor, the computing device associated with the user to generate a consumable preference questionnaire; receiving, by the processor, from the computing device associated with the user, answers to the consumable preference questionnaire; and generating, by the processor, the daily score intake value associated with the user based, at least in part on, on the answers to the consumable preference questionnaire.

In some aspects, the techniques described herein relate to a method, further including utilizing, by the at least one processor, at least one consumable item intake score based at least in part on the at least one first nutrient amount and the at least on second nutrient amount.

In some aspects, the techniques described herein relate to a method, further including: receiving, by the at least one processor, at least one consumption indication indicative of the user having consumed the at least one consumable item; and updating, by the at least one processor, the daily score intake value by deducting the at least one consumable item intake score in response to the at least one consumption indication.

In some aspects, the techniques described herein relate to a computer-based system including: at least one processor in communication with at least one non-transitory computer readable medium having software instructions stored thereon, wherein, upon execution of the software instructions, the at least one processor is configured to: receive, from a computing device associated with a user, at least one consumable preference associated with the user; wherein the at least one consumable preference identifies the at least one food category, the at least one beverage category or a combination thereof; receive a daily score intake value associated with the user; obtain a content data regarding at least one consumable item; wherein the at least one consumable item is at least one food item, at least one beverage item, or a combination thereof; wherein the content data includes a first content data item identifying at least one first amount of at least one first nutrient found in the at least one consumable item; automatically apply, in real-time, a nutrient prediction machine learning model to the content data regarding the at least one consumable item to predict at least one second amount of at least one second nutrient in the at least one consumable item based at least in part on: i) the first content data item identifying the at least one first amount of the at least one first nutrient found in the at least one consumable item, ii) the second content data item identifying the at least one second nutrient having the at least one second amount found in the at least one consumable item, and iii) a decision tree library of at least one thousand nutrient decision trees; determine at least one zero-scored consumable item based, at least in part, on: i) the daily score intake value associated with the user, ii) the at least one first amount of the at least one first nutrient, iii) the at least one second amount of the at least one second nutrient, and iv) the at least one consumable preference; and instruct the computing device associated with the user to utilize at least one graphical user interface element to identify the at least one zero-scored consumable item on a screen of the computing device.

In some aspects, the techniques described herein relate to a system, wherein the nutrient prediction machine learning model includes a decision tree model having a subset of decision trees from the decision tree library; wherein each decision tree of the subset of decision trees includes a plurality of branches and a plurality of leaves; and wherein the decision tree model is trained to form each branch of the plurality of branches based at least in part on learned threshold values of nutrient quantities.

In some aspects, the techniques described herein relate to a system, wherein, upon execution of the software instructions, the at least one processor is further configured to: select the subset of decision trees from the decision tree library based at least in part on the content data; apply each decision tree in the subset of decision trees to the content data to predict the at least one decision tree-specific second amount of the at least one second nutrient in the at least one consumable item based at least in part on: i) the first content data item identifying the at least one first amount of the at least one first nutrient found in the at least one consumable item, and ii) the second content data item identifying the at least one second nutrient having the at least one decision tree-specific second amount found in the at least one consumable item; and aggregate the at least one decision tree-specific second amount of each decision tree to produce the at least one second amount.

In some aspects, the techniques described herein relate to a system, wherein, upon execution of the software instructions, the at least one processor is further configured to: receive at least one known second amount representative of at least one actual amount of the at least one second nutrient in the at least one consumable item; determine at least one second nutrient prediction error based at least in part on a different between the at least one second amount and the at least one known second amount; and update the learned threshold values of nutrient quantities of each branch of the plurality of branches of each decision tree in the subset of decision trees based at least in part on the at least one second nutrient prediction error.

In some aspects, the techniques described herein relate to a system, wherein, upon execution of the software instructions, the at least one processor is further configured to prune the subset of decision trees based at least in part on the at least one second nutrient prediction error.

In some aspects, the techniques described herein relate to a system, wherein, upon execution of the software instructions, the at least one processor is further configured to: select the subset of decision trees from the decision tree library based at least in part on model parameters; receive at least one known second amount representative of at least one actual amount of the at least one second nutrient in the at least one consumable item; determine at least one second nutrient prediction error based at least in part on a different between the at least one second amount and the at least one known second amount; and update the model parameters based at least in part on the at least one second nutrient prediction error.

In some aspects, the techniques described herein relate to a system, wherein the nutrient prediction machine learning model includes a random forest.

In some aspects, the techniques described herein relate to a system, wherein, upon execution of the software instructions, the at least one processor is further configured to: instruct the computing device associated with the user to generate a consumable preference questionnaire; receive from the computing device associated with the user, answers to the consumable preference questionnaire; and generate the daily score intake value associated with the user based, at least in part on, on the answers to the consumable preference questionnaire.

In some aspects, the techniques described herein relate to a system, wherein, upon execution of the software instructions, the at least one processor is further configured to utilize at least one consumable item intake score based at least in part on the at least one first nutrient amount and the at least on second nutrient amount.

In some aspects, the techniques described herein relate to a system, wherein, upon execution of the software instructions, the at least one processor is further configured to: receive at least one consumption indication indicative of the user having consumed the at least one consumable item; and update the daily score intake value by deducting the at least one consumable item intake score in response to the at least one consumption indication.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may.

Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

Figure 1A:
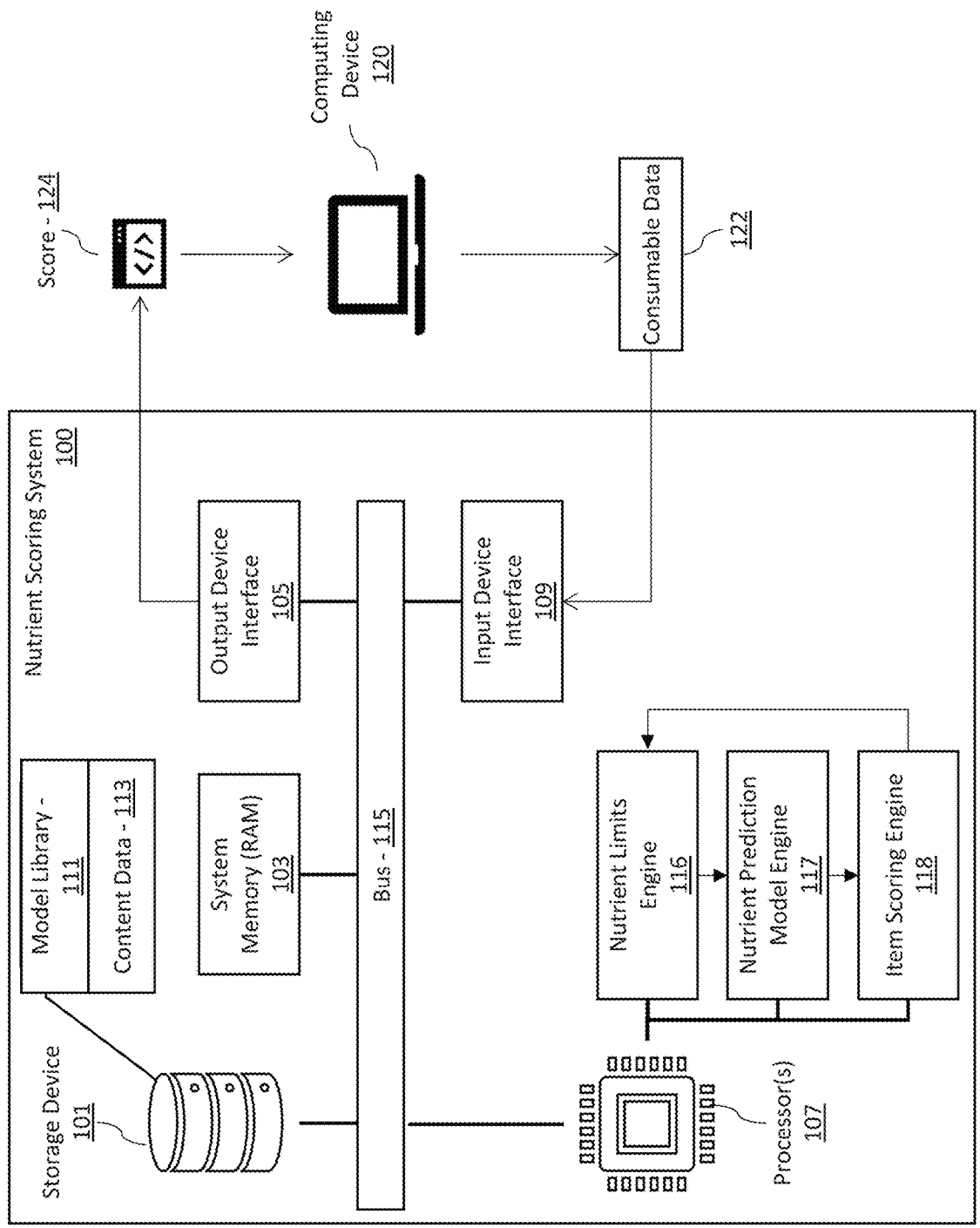
FIG. 1A and FIG. 1B are a block diagrams of a computer-based nutrient scoring system 100 in accordance with one or more embodiments of the present disclosure.
Figure 1B:
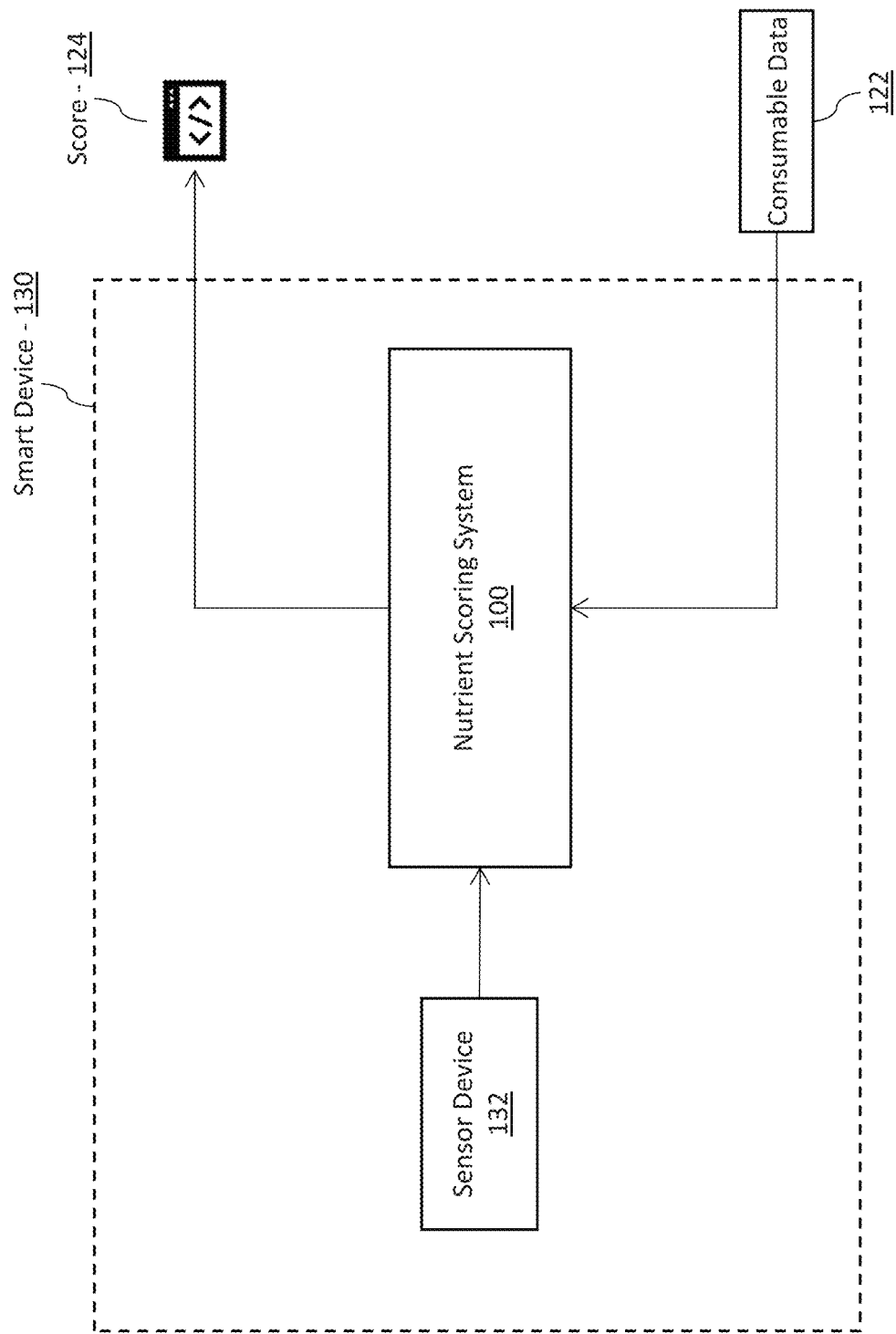

FIGS. 1A and 1B are a block diagrams of a nutrient scoring system 100 for more accurate and efficient diet planning and weight management in accordance with one or more embodiments of the present disclosure.

In some embodiments, users can interact with a nutrient scoring system 100 to manage diet and weight accurately and effectively. In some embodiments, users may employ a computing device 120 to provide consumable data 122 to the nutrient scoring system to track dietary and consumable habits using an easy to understand score system. The score system scores the impact of particular consumable items on a budget of score values ("score budget") that is customized for the user. Accordingly, in some embodiments, each consumable item consumed by a user may be input via the computing device 120 and communicated to the nutrient scoring system 100. In some embodiments, the nutrient scoring system 100 may determine a score value for the consumable item and apply the value to the user's score budget. Upon doing so, the nutrient scoring system 100 may output to the computing device 120 the item score 124 signifying the score value of the consumable item and/or the remaining score in the user's score budget based on the score value of the consumable item.

In some embodiments, a user may earn score values to increase the score budget by consuming healthy foods and beverages, such as vegetables and water. For example, for every, e.g., 1 cup serving of non-starchy vegetables the user may earn 1 Daily Value toward the score budget, and for reaching a daily water goal of X fl oz the user may earn up to 1 Daily Value toward the score budget. In some embodiments, the score value added to or deducted from the score budget may account for various nutrients and use calculated calories for an accurate base value.

In some embodiments, specific factors of consumables that may raise the score value of a particular consumable may include, e.g., calories, saturated fat, added sugar, or other nutrients that have a negative association on health and weight management. Conversely, factors of consumables that may reduce the score value of a particular consumable may include protein, fiber, unsaturated fat or other nutrients that have a positive association on health and weight management.

However, the quantity of certain nutrients, such as added sugar, trans fat, saturated fat, etc., in consumables may be difficult to ascertain in some regions, the nutrient scoring system 100 may employ a data science model that predicts the quantity of these nutrients with high accuracy to fill in gaps in nutritional information.

Accordingly, in some embodiments, the consumable data 122 may be communicated to the nutrient scoring system 100 via an input device interface 109. In some embodiments, the input device interface 109 may include, e.g., a suitable hardware and/or software interface, such as, e.g., Universal Serial Bus (USB), wired or wireless network connections (e.g., WiFi, Bluetooth, Zigbee, Z-Wave, etc.), application programming interface (API), or other suitable interfacing technology or any combination thereof.

In some embodiments, the nutrient scoring system 100 may receive the consumable data 122 to determine a score 124 of consumed food items, such as, e.g., fruits, vegetables, baked goods, beverages, alcohol, meats, fish, poultry, among other consumables or any combination thereof. In some embodiments, the nutrient scoring system 100 may be a part of the computing device 120. Thus, the nutrient scoring system 100 may include hardware and software components including, e.g., computing device 120 hardware and software, cloud or server hardware and software, or a combination thereof.

Accordingly, in some embodiments, the nutrient scoring system 100 may be implemented in any suitable computing system for receiving consumable data 122, determining a maximum score budget, generating and running a machine learning model for determining nutrient quantities and score consumable items to output the score 124. In some embodiments, the computing system may include, e.g., a remote computing system such as, e.g., a cloud computing service, one or more servers, a mainframe, a remote desktop, virtual machine, software container, or other computing system positioned remote from the computing device 120. In some embodiments, the computing system may include a local computing system, such as, e.g., processing and/or memory resources of the computing device 120 (e.g., via a native application, virtual machine, or other software run remotely to implement the nutrient scoring system 100), or any suitable computing device connected, via a wired and/or wireless connection, to the computing device 120. For example, in some embodiments, the nutrient scoring system 100 may be implemented in an embedded system, such as, e.g., a smart device and/or Internet-of-Things (IoT) device, such as, e.g., a smart scale for weighing consumable items, a smart oven, a smart microwave, a smart stove, a smart refrigerator, or other internet connected and/or processing system embedded device to receive consumable data 122, determine a maximum score budget, generate and running a machine learning model for determine nutrient quantities and score consumable items to output the score 124.

In some embodiments, the nutrient scoring system 100 may include hardware components such as a processor(s) 107, which may include local or remote processing components. In some embodiments, the processor(s) 107 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor(s) 107 may include data-processing capacity provided by the microprocessor. In some embodiments, the microprocessor may include memory (e.g., system memory (RAM) 103), processing, interface resources, controllers, and counters. In some embodiments, the microprocessor may also include one or more programs stored in memory.

Similarly, the nutrient scoring system 100 may include storage device 101, such as local hard-drive, solid-state drive, flash drive, database or other local storage, or remote storage such as a server, mainframe, database or cloud provided storage solution.

In some embodiments, the nutrient scoring system 100 may implement computer engines for generating nutrient limits such as a daily or weekly score budget for a user, for generating a customized model for consumable item, for applying the customized model to predict a nutrient quantity, to determine a score value for the consumable item, among other functionalities or any combination thereof. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, to determine the score budget of a user, the nutrient scoring system 100 may include computer engines including, e.g., a nutrient limits engine 116. In order to implement the nutrient limits engine 116, the nutrient limits engine 116 may include dedicated and/or shared software components, hardware components, or a combination thereof. For example, the nutrient limits engine 116 may include a dedicated processor and storage. However, in some embodiments, the nutrient limits engine 116 may share hardware resources, including the processor(s) 107 and storage device 101 of the nutrient scoring system 100 via, e.g., a bus 115.

In some embodiments, the nutrient limits engine 116 may associate the user with consumable preferences of the user, e.g., in a user profile or other user data storage. For example, in some embodiments, the user may have a user profile identified according to a profile identifier (e.g., account name, account number, telephone number, email address, or any other mechanism for indexing user profiles). The user at the computing device 120 may log into the user profile using the profile identifier and access consumable preferences associated with the user, e.g., stored in the user profile in the storage device 101. Alternatively, the nutrient limits engine 116 may receive from the computing device 120 user selected or user input consumable preferences.

In some embodiments, the consumable preferences may include one or more consumable preferences that relate to preferred frequency of consuming a corresponding consumable item, such as a food item or beverage. For example, the consumable preference(s) may include a frequency on an average week that the user consumes, e.g., vegetables, starches, alcohol, fruits, meats, fish, soda, water, or other food category and/or beverage category or any combination thereof.

In some embodiments, based on the consumable preference(s) of the user, the nutrient limits engine 116 may determine a daily score intake value associated with the user using one or more formulas. For example, the nutrient limits engine 116 may include a scoring formula that includes the following nutrient variables: calories, saturated fat, sugar, protein, and alcohol, and includes two steps:

In some embodiments, Step 1: Calculate value equivalent calories (VEC):

$$\text{Value Equivalent Calories} = \frac{([\text{Calculated Calories}] * 1.01 + [SatFat(gm) * 9.7] + [\text{Natural Sugar}(gm)] * 0.9 + [\text{Added Sugar}(gm)] * 4.5 + [\text{Alcohol}(gm)] * 0.2 - [\text{Protein}(gm)] * 2.7 - [\text{Rewardable Fiber}(gm)] * 9.3 - [Unsat\ \text{Fat}(gm)] * 1.2) * 0.8]}{\text{Weight}(gm)\text{per serving}}$$

Where Svg is defined by the reference value to which the nutrition facts refer, and the amount of food consumed.

Step 2: calculate the score:

In some embodiments of the weight management control method of the present invention, the unrounded VE is multiplied by the amount of consumed food. In some embodiments, the unrounded product (VE×serving size) is divided with the denominator 33, yielding unrounded score. In some embodiments, if the unrounded score value has a decimal value equal to or less than 0.49, the score value is rounded down to the nearest whole number (e.g., but not limited to, unrounded Score=1.49=1). In some embodiments, if the unrounded score value has a decimal value equal to or greater than 0.50, the unrounded score value is rounded up to the nearest whole number (e.g., unrounded score value=1.50=2). In some embodiments, the equation below illustrates the calculation of the score value:

$$\text{Score} = \frac{\text{Value Equivalent Calories(result of step 1)}}{29(\text{Denominator})} * \text{Serving Size}$$

In some embodiments, the rounding step occurs once in the final step in the score value calculation.

EXAMPLE

Score Calculation in Consumer-Facing Calculator Tools

In some embodiments of the weight management control method of the present invention, examples of consumer-facing calculator tools are, but are not limited to, online, mobile, offline calculator, barcode scanner tools. In some embodiments, a simplified formula is used in these environments, where the formula excludes alcohol as a variable. In some embodiments, the simplified calculation applies to all tools that allow users to calculate a score value using a Nutrition Facts Label. In some embodiments, the labeling legislation for the US and EU does not include nutritional data for alcoholic beverages. In some embodiments, grams of alcohol are not always available to consumers, as such information is not mandated to be provided on all Nutrition Facts labels.

EXAMPLE

Score Target and Allowance Calculations

In some embodiments of the weight management control method of the present invention, a user's allotted score include a Daily Score Target (DST) and Weekly Score Allowance (WSA). In some embodiments, score allotment calculations are derived from Total Energy Expenditure (TEE). In some embodiments, the TEE can include a multiplier (e.g., but not limited to, a low activity multiplier), where the multiplier accounts for an activity level (e.g., but not limited to, the user's activity level). In some embodiments, an activity multiplier can range from 1.1-2.0, where the range from 1.1-2.0 includes a range of activity levels, from people who maintain a sedentary lifestyle to people who maintain an active lifestyle. In some embodiments, the low activity multiplier is 1.3, where the low activity multiplier is used in connection with a person having a substantially sedentary lifestyle. In some embodiments, the TEE is calculated individually based on Mifflin et al. (see e.g., MD Mifflin, ST St Jeor, et al. A new predictive equation for resting energy expenditure in healthy individuals, Am J Clin Nutr. 1990 Fe; 51(2):241) with an adjustment for activity.

The table below shows some embodiments of the weight management control method of the present invention, including TEE variables, rounding rules and conversion factors:

| Variable | Point of measure | Equation to use |
| --- | --- | --- |
| Gender | MALE/ FEMALE | n/a |
| Age | Years | Round to the nearest whole number, e.g. 42 years |
| Height | Centimeters | Round to the nearest whole number, e.g. 175 cm<br>Conversion factors metric & imperial system:<br>1 inch(in) = 2.54 centimeters (cm) |
| Weight | Kilograms (kg) | Round to the nearest tenth value, e.g. 70.5 kg<br>Conversion factors metric & imperial system:<br>1 pound (lb.) = 453.59 grams (g) = 0.4539 kilograms (kg)<br>kg*2.2046 = lb.<br>lb.*0.4536 = kg |

EXAMPLE

Daily Score Target (DST)

In some embodiments of the weight management control method of the present invention, the Daily Score Target (DST) is calculated using TEE and/or the Mifflin parameters, includes a daily calorie deduction of 1000 calories per individual, a minimum and a maximum daily calorie cap, a general deduction of between 100-500 calories to cover zero-scored food consumption (fruits and vegetables), calculated by dividing the daily calorie budget by 31, which represents the Average Actual Equivalent per score (AACE), in digital products the DST is calculated automatically when a new weight is entered, or any combination thereof. In some embodiments, the general deduction is between 200-500 calories to cover "zero-scored food". In some embodiments, the general deduction is between 300-500 calories to cover "zero-scored food". In some embodiments, the general deduction is between 400-500 calories to cover "zero-scored food". In some embodiments, the general deduction is between 100-400 calories to cover "zero-scored food". In some embodiments, the general deduction is between 100-300 calories to cover "zero-scored food". In some embodiments, the general deduction is between 100-200 calories to cover "zero-scored food". In some embodiments, the general deduction is between 200-400 calories to cover "zero-scored food". In some embodiments, the general deduction is between 200-300 calories to cover "zero-scored food". In some embodiments, the general deduction is between 300-400 calories to cover "zero-scored food". In some embodiments, fresh fruits/vegetables and frozen fruits/vegetables are considered "zero-scored food." In some embodiments, dried fruits/vegetables and/or fruits/vegetables stored in, for example, syrup, are not considered "zero-scored food". In some exemplary non-limiting embodiments, potatoes, avocadoes, and corn are not considered "zero-scored foods." The table below illustrates a non-limiting example of min/max cap of some embodiments of the present invention, where the multiplier 1.3. In some embodiments, the multiplier correlates with the activity level of the user, and can range from 1.2 to 1.4 (e.g., but not limited to, 1.2-1.3, 1.3-1.4, 1.25-1.35, etc.):

| | DST Calculation | |
|---|---|---|
| Step | Equation | Notes & Rules |
| 1. | TEE MEN (low activity multiplier):<br>[10 × weight (kg) + 6.25 × height (cm) − 5 × age (y) + 5] × 1.3<br>TEE WOMEN (low activity multiplier):<br>[10 × weight (kg) + 6.25 × height (cm) − 5 × age (y) − 161] × 1.3 | Brackets are taken into account in the calculation |
| 2. | TEE − 1000 calories | ⇨ minimum cap:<br>IF: TEE − 1000 < 1000<br>THEN: use 1000 for next calculation steps<br>⇨ maximum cap:<br>IF: TEE − 1000 > 1800<br>THEN: use 1800 for next calculation steps |
| 3. | [Result from step 2] − 200 calories | |
| 4. | [Result from step 3]/31 | |
| 5. | [Result from step 4] round to the nearest whole number = DST | |

The table below illustrates an overview of DST calculation of some embodiments of the present invention:

| | DST Calculation | |
|---|---|---|
| Step | Equation | Notes & Rules |
| 1. | TEE MEN(low activity multiplier):<br>[10 × weight (kg) + 6.25 × height (cm) − 5 × age (y) + 5] × 1.3<br>TEE WOMEN(low activity multiplier):<br>[10 × weight (kg) + 6.25 × height (cm) − 5 × age (y) − 161] × 1.3 | Brackets are taken into account in the calculation |
| 2. | TEE − 1000 calories | ⇨ minimum cap:<br>IF: TEE − 1000 < 1131<br>THEN: use 1100 for next calculation steps<br>⇨ maximum cap:<br>IF: TEE − 1000 > 1800<br>THEN: use 1800 for next calculation steps |
| 3. | [Result from step 2] − 200 calories | |
| 4. | [Result from step 3]/31 | |
| 5. | [Result from step 4] round to the nearest whole number = DST | |

EXAMPLE

Weekly Score Allowance (WSA)

In some embodiments of the weight management control method of the present invention, the Weekly Score Allowance (WSA) is determined using the actual daily energy deficit (i.e., recommended calorie intake minus estimated caloric expenditure) and, in digital products, the WSA is calculated automatically when a new weight is entered.

The table below illustrates WSA calculation of some embodiments of the present invention:

| | WUA Calculation | |
|---|---|---|
| Step | Equation | Notes & Rules |
| 1. | TEE MEN (low activity multiplier): [10 × weight (kg) + 6.25 × height (cm) − 5 × age (y) + 5] × 1.3  TEE WOMEN (low activity multiplier): [10 × weight (kg) + 6.25 × height (cm) − 5 × age (y) − 161] × 1.3 | Ensure brackets are taken into account in the calculation! |
| 2. | TEE − 1000 calories | ⇨ minimum cap: IF: TEE − 1000 < 1000 THEN: use 1000 for next calculation steps  ⇨ maximum cap: IF: TEE − 1000 > 1800 THEN: use 1800 for next calculation steps |
| 3. | TEE − [Result of Step 2] | This includes the minimum and the maximum cap. E.g. if Step 1 resulted in a value of 1650 and step 2 resulted in a value of 1000 (because minimum in place), the value of Step 3 would be 650 |
| 4. | If the result of Step 3 is: ≤250, WSA = 14 >250 and ≤500, WSA = 21 >500 and ≤750, WSA = 28 >750 and <1000, WSA = 35 ≥1000, WSA = 42 | |

EXAMPLE

Daily Score Target for Nursing Mothers

In some embodiments of the weight management control method of the present invention, nursing mothers may use the present weight management control method no earlier than one month post childbirth. In some embodiments, a breastfeeding mother increases the daily calorie intake by 400 calories per day (compared to a non-breastfeeding woman), i.e., a minimum of daily calorie intake is 1800 kcal, and the maximum energy deficit of 600 kilocalories per day.

The table below shows the DST calculation for nursing mothers ("mums") for some embodiments of the present invention:

| | DST Calculation-Nursing Mums | |
|---|---|---|
| Step | Equation | Notes & Rules |
| 1. | TEE WOMEN breastfeeding (low activity multiplier): [10 × weight (kg) + 6.25 × height (cm) − 5 × age (y) − 161] × 1.3 | Ensure brackets are taken into account in the calculation |
| 2. | TEE + 400 − 600 calories | ⇨ minimum cap: IF: TEE + 400 − 600 < 1800 THEN: use 1800 for next calculation steps  ⇨ maximum cap: IF: TEE − 1000 > 3069 THEN: use 3069 for next calculation steps |
| 3 | [Result from step 2] − 200 calories | n/a |
| 4 | [Result from step 3]/31 | |
| 5 | [Result from step 4 ]round to the nearest whole number = DPA | |

In some embodiments, the WSA calculation is the same for nursing mothers and women (as described in Example: Weekly Score Allowance (WSA) above).

EXAMPLE

Activity Values Calculation

In some embodiments of the weight management control method of the present invention, the formulas for new Activity Score are provided below:

Low intensity Activity Score:

$$\frac{[(67\times.1)+3.5]\times.005\times \text{kg body weight}\times \text{minutes}}{[A]} = X$$

Moderate intensity Activity Score:

$$\frac{[(107.2\times.1)+3.5]\times.005\times \text{kg body weight}\times \text{minutes}}{[A]} = Y$$

High intensity Activity Score:

$$\frac{[(160.8\times.2)+3.5]\times.005\times \text{kg body weight}\times \text{minutes}}{[A]} = Z$$

In some embodiments of the weight management control method of the present invention, "A" is between 30-70. In some embodiments, "A" is between 30-60. In some embodiments, "A" is between 30-50. In some embodiments, "A" is between 30-40. In some embodiments, "A" is between 40-70. In some embodiments, "A" is between 50-70. In some embodiments, "A" is between 60-70. In some embodiments, "A" is between 40-60. In some embodiments, "A" is between 40-50. In some embodiments, "A" is between 50-60. In some embodiments, "A" is any exact point in any of the ranges herein, e.g., but not limited to, between the range of 40-50, e.g., 40, 41, 42, 43, 44, 45, 46, 47, 48, 49, and 50, etc. In some embodiments, "A" is any exact point in any of the ranges herein, e.g., 35, 45, 55, etc.

EXAMPLE

Zero Scored Foods

In some embodiments of the weight management control method of the present invention, certain foods are identified as having a score of zero ("zero scored foods") which may account for such foods, for example, but not limited to, fresh/frozen fruits and vegetables when eaten in meals and recipes (excluding dried fruits/vegetables, potatoes, etc. as described herein). In some embodiments, the designation of zero scored foods may be applied to food labels, publications, magazines, books, programs, and website content, among other places or any combination thereof to alert users to zero scored food items. In some embodiments, an exception to counting fruits and/or vegetables as zero scored foods may include where fruits and/or vegetables are used to prepare beverages or liquid meals, e.g., juices or smoothies, and instead the fruit and/or vegetable nutrient content will be applied to a formula as disclosed herein.

EXAMPLE

"No Count" Option

In some embodiments, the weight management control method of the present invention includes a 'non-tracking' option based on limiting the food choices to wholesome and mostly unprocessed foods. In some embodiments, the 'non-tracking' option can be utilized as a recovery plan with coaching.

In some embodiments, the DSA and/or WSA may be used to determine the score budget that is customized for the user. Thus, for each consumable item that the user tracks, the consumable data 122 may be used to add or subtract from the score budget, where the score budget signifies the number of score values of consumable items allotted to maintain a healthy diet. Accordingly, in some embodiments, the nutrient scoring system 100 may determine the number of score values associated with consumable data 122 with which to modify the user's score budget.

In some embodiments, the consumable data 122 may include nutritional information, such as, e.g., the quantity (e.g., in calories, kilocalories ("Calories"), grams, kilograms, micrograms, ounces, pounds, fluid ounces, etc.) of one or more nutrients in a consumable item associated with the consumable data 122. However, nutritional information does not always include data for each nutrient that affects the score budget. For example, fiber and added sugar as opposed to total sugar or total carbohydrates is not always specified or available. Similarly, fat content may not be specified according to saturated fats, unsaturated fats and trans-fat. Therefore, accurately tracking the effect on consumables that do not have available the quantity of added sugar, fiber, trans fats, unsaturated fats, or other nutrients or any combination thereof results in incomplete data for determining the score value of the consumable item. In an equation with two unknown values, we cannot use a static equation to determine the value of added sugar or fiber. We use a machine learning model to capture nonlinear relationships in the data instead.

In some embodiments, to infer the amount of the missing nutrient (e.g., added sugar, fiber, fat, etc.), the nutrient scoring system 100 may include computer engines including, e.g., a nutrient prediction model engine 117. In order to implement the nutrient prediction model engine 117, the nutrient prediction model engine 117 may include dedicated and/or shared software components, hardware components, or a combination thereof. For example, the nutrient prediction model engine 117 may include a dedicated processor and storage. However, in some embodiments, the nutrient prediction model engine 117 may share hardware resources, including the processor(s) 107 and storage device 101 of the nutrient scoring system 100 via, e.g., a bus 115.

In some embodiments, the nutrient prediction model engine 117 may identify from the consumable data 122 the consumable item selected or otherwise input by the user via the computing device 120. In some embodiments, the consumable data 122 may include nutritional information and other consumable item information, such as, e.g., a consumable item name, a consumable item category (e.g., food category and/or beverage category), each nutrient in the consumable item, a quantity of each nutrient, among other data related to the consumable item. In some embodiments, the consumable data 122 may include an amount of the consumable item consumed and/or a serving size of the consumable item.

In some embodiments, some or all of the information related to the consumable item may be stored in the storage device 101. Accordingly, the consumable data 122 may include, e.g., a consumable name and a consumable quantity consumed by the user. The nutrient prediction model engine 117 may then cross-reference the consumable item name in the storage device 101 to identify content data 113 storing consumable information (e.g., nutrients and nutrient quantities, portion size, etc.) in the content data 113 stored in the storage device 101.

In some embodiments, missing nutrient quantities may be inferred based on the consumable and the quantities of other nutrients in the consumable. Accordingly, the nutrient prediction model engine 117 may use the content data 113 and/or the consumable data 122 to generate and apply a machine learning model for predicting unknown nutrient quantities. In some embodiments, the storage device 101 may include a model library 111 storing one or more trained machine learning models trained to predict a quantity of an associated nutrient. In some embodiments, each trained machine learning model may be custom trained for a particular food and/or beverage category, or the training machine learning models may be general to any food and/or beverage category. Accordingly, the nutrient prediction model engine 117 may identify a missing nutrient in the content data 113 and/or consumable data 122 and select from the model library 111 the associated trained machine learning model.

In some embodiments, the nutrient prediction model engine 117 may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neural network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:
  a. define Neural Network architecture/model,
  b. transfer the input data to the exemplary neural network model,
  c. train the exemplary model incrementally,
  d. determine the accuracy for a specific number of timesteps,
  e. apply the exemplary trained model to process the newly-received input data,
  f. optionally and in parallel, continue to train the exemplary trained model with a predetermined periodicity.

In some embodiments and, optionally, in combination with any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination with any embodiment described above or below, an output of the exemplary aggregation function may be used as input to the exemplary activation function. In some embodiments and, optionally, in combination with any embodiment described above or below, the bias may be a constant value or function that may be used by the aggregation function and/or the activation function to make the node more or less likely to be activated.

In some embodiments, the nutrient prediction model engine 117 may load the selected trained machine learning model and instantiate the trained machine learning model in order to automatically generate a consumable-specific machine learning model in response to receiving the consumable data 122.

In some embodiments, the model library 111 may include trained decision trees. While any suitable machine learning model for predicting a quantity may be employed, decision-tree based models, such as a decision tree depicted in FIG. 6, may be an efficient and accurate model architecture for determining a likely value of a missing nutrient. In some embodiments, the model library 111 may include multiple decision trees, such as, e.g., hundreds, thousands, tens of thousands, hundreds of thousands, millions or more decision trees that may be stacked to improve the accuracy and/or generalizability of estimates of missing nutrients. For example, multiple decision trees may be selected from the model library 111 based on the consumable data 122 and/or the content data 113 and the nutrient prediction model engine 117 may stack the selected decision trees, e.g., via averaging, summing, weighted averaging, weighted summing, or other aggregation or any combination thereof, to produce a machine learning model for use in inferencing (e.g., see for example FIG. 7).

In some embodiments, the nutrient prediction model engine 117 may construct a particular trained machine learning model by stacking multiple trees. Each decision tree, built via the above process, is prone to over-specification, where it too closely matches the underlying training data. In this case the model will not generalize effectively for un-seen data score during inference. In some embodiments, to avoid this, the stacking of multiple trees can be used. In some embodiments, the stacking can occur in two ways, the first way a so called "random forest" is created where the nutrient prediction model engine 117 constructs each tree using a random subset of available consumable data 122 and/or content data 113. The predictions from each resulting tree are averaged for an inference result, e.g., a nutrient quantity. In some embodiments, in the second way, so called gradient-boosted trees, the nutrient prediction model engine 117 builds trees sequentially, where each subsequent tree has a target nutritional value which represents the difference between the true-result and the result that was predicted by the previous tree. In this way, gradient-boosted trees are iteratively focusing on reducing the predictions which have the largest error toward ground truth.

In some embodiments, to create the trees of the nutrient prediction machine learning model, the nutrient prediction model engine 117 may be used to train a decision tree model via branching based on known pairings of listed nutrients quantities and unlisted nutrient quantities as described below with respect to FIG. 4. The branching is part of the decision tree building process, which is the training process. The inference process simply takes input nutrient data and follows each branch of the tree toward each tree's terminal node. Each terminal node represents some contribution to the final prediction which is the output of the model.

In some embodiments, the nutrient prediction model engine 117 may create the decision trees during training using a greedy optimization process. The training process encompasses the branching process, but it also includes a pruning process.

In some embodiments, the branching process has several parts to it, firstly, one of the feature-dimensions (in our case, one of the existing, known nutrient values) is chosen to create a branch. This selection process varies according to the model's parameterization. It could come from a random subset of all possible nutrient values, or it could be selected from all possible nutrient values. The selection can also be based on the optimality of the performance for a branch based on each individual nutrient value.

In some embodiments, branch splitting criteria and performance is based on choosing a threshold within a single nutrient value. In some embodiments, the branch will then split all of the predicted target nutrients to be less than, or greater than or equal to, the threshold. In this case, all target nutrient values on either side of the threshold are aggregated into an average, which represents the decision tree predicted nutrient value for that "leaf" resulting from the threshold choice. The threshold is iteratively evaluated to find the optimal location, which produces the lowest mean-squared error between predictions resulting from the split choice on each particular branching variable.

In some embodiments, this branching process will be repeatedly applied, adding more leaves, and thereby creating more aggregated predicted values for the target nutrient across each leaf. The process stops when a predefined target criteria are met, such as a limiting depth, or a minimum number of existing target nutrient data score to aggregate within the potential leaf.

In some embodiments, after branching, during training the nutrient prediction model engine 117 may perform a "pruning" operation. While branching occurs by building a tree from the top-down, pruning works from a bottom up traversal. Each node is visited upwards after building to determine if removing or pruning the branch would ultimately create a lower mean-squared error in the totality of the resulting leaves. This controls the complexity of the decision tree being built.

In some embodiments, the nutrient prediction model engine 117 may also identify, based on the consumable data 122 and/or content data 113, optimal locations in each decision tree to produce branches to stack decisions trees and produce the consumable-specific machine learning model.

In some embodiments, the nutrient prediction model engine 117 may ingest the consumable data 122 and/or the content data 113, including e.g., the food category and/or beverage category, the quantity of each nutrient of the known nutrients, a portion size or serving size, a number of calories of per serving size or portion size, among other consumable information. The consumable-specific machine learning model may process the consumable data 122 and/or the content data 113 and automatically output a quantity for the missing nutrient to predict the missing nutrient.

In some embodiments, to determine an impact of the consumable item on the user's score budget of food score values, the nutrient scoring system 100 may include computer engines including, e.g., an item scoring engine 118. In order to implement the item scoring engine 118, the item scoring engine 118 may include dedicated and/or shared software components, hardware components, or a combination thereof. For example, the item scoring engine 118 may include a dedicated processor and storage. However, in some embodiments, the item scoring engine 118 may share hardware resources, including the processor(s) 107 and storage device 101 of the nutrient scoring system 100 via, e.g., a bus 115. In some embodiments, the item scoring engine 118 may use the quantity of each nutrient, including the predicted quantity output by the nutrient prediction model engine 117 to determine a score value for the consumable item.

In some embodiments, the score value may be fed back to the nutrient limits engine 116 to determine a modified score budget. For example, where the consumable item is a tracked food item consumed by the user, the score budget may be altered to reflect the real-time use of or addition to the score in the score budget. Alternatively, or in addition, the consumable data 122 may be a consumable preference in setting the score budget of food score values. Accordingly, the nutrient limits engine 116 may use the score budget, the quantity of each known nutrient and the predicted quantity of the unknown nutrient and/or the score value of the consumable item to determine one or more zero scored consumable items.

In some embodiments, the zero scored consumable item is an item for which the score budget is designed to compensate. For example, where a consumable preference of the user is to consume a particular consumable or category of consumable at a desired frequency, the nutrition limits engine 116 may determine the score budget assuming a frequency of consuming the particular consumable or category of consumable. Thus, the particular consumable or category of consumable may be set as a zero scored consumable such that upon the user consuming and tracking an item of the particular consumable or category of consumable, there is no deduction from or addition to the score budget.

In some embodiments, upon determining the score value of the consumable item and/or the score budget, the nutrient scoring system 100 may communicate, e.g., via an output device interface 105, a score 124 to the computing device 120. In some embodiments, the score may include a current score budget based on tracked consumable items, a score value for a tracked consumable item, or any combination thereof. In some embodiments, the score 124 may be displayed to the user via a graphical user interface and/or element(s) thereof upon instruction by the nutrient scoring system 100. In some embodiments, the nutrient scoring system 100 may additionally communicate the zero scored consumable item(s) and instruction to the computing device 120 to display the zero scored consumable item(s) via the graphical user interface and/or element(s) thereof.

In some embodiments, one or more of the nutrient limits engine 116, the nutrient prediction model engine 117, the nutrient prediction model engine 117, the item scoring engine 118, the model library 111 and the content data 113 may be implemented in a smart device (e.g., an IoT or embedded device as described above or any other suitable "smart" device). Thus, a user may use the smart device 130, e.g., in the preparation and/or selection or a consumable item, and the smart device may provide information about the consumable item including content data 113 and the score 124. In some embodiments, the smart device 130 may use the consumable data 122 and a sensor device 132 to determine characteristics of the consumable item, such as, e.g., weight, volume, count, how well cooked (e.g., done, well done, very well done, underdone, rare, medium, well, etc.), label contents, or other characteristics or any combination thereof.

For example, in some embodiments, the smart device 130 may be a smart scale that is used to measure consumable item weight as a kitchen or baking scale. The smart scale may include computing resources such as the processor(s)

107 and storage device 101, the RAM 103, the output device interface 105 and the input device interface 109, among other computing resources, to score each consumable item based on weight. Accordingly, in some embodiments, the user may input consumable data 122 including a type and/or name and/or category of the consumable item to the nutrient scoring system 100. In some embodiments, the user may input the consumable data 122 using, e.g., via the input device interface 109, the computing device 120, a keyboard, a touchscreen, one or more buttons or touch-sensitive switches, or other input device connected to the input device interface 109 or any combination thereof.

In some embodiments, the smart scale may include a sensor device 132 including a weight sensor. Accordingly, the user may then place the consumable item on the sensor device 132 to determine a weight thereof in, e.g., ounces, grams, kilograms, pounds, etc. Based on the consumable data 122 and the weight, the nutrient scoring system 100 may determine a score 124 according to a quantity of various nutrients as described above. As a result, the nutrient scoring system 100 may output the score 124 based upon the weight of the consumable item.

In another example, the smart device 130 may include, e.g., a smart microwave oven. The smart microwave may include computing resources such as the processor(s) 107 and storage device 101, the RAM 103, the output device interface 105 and the input device interface 109, among other computing resources, to score each consumable item based on the microwave heating of the consumable item. Accordingly, in some embodiments, the user may input consumable data 122 including a type and/or name and/or category of the consumable item to the nutrient scoring system 100. In some embodiments, the user may input the consumable data 122 using, e.g., via the input device interface 109, the computing device 120, a keyboard, a touchscreen, one or more buttons or touch-sensitive switches, or other input device connected to the input device interface 109 or any combination thereof.

In some embodiments, the smart microwave may include a sensor device 132 including a microwave power and microwave time sensor. Accordingly, the user may then place the consumable item in the smart microwave to warm and/or cook the consumable item, and the microwave power and/or microwave time from the sensor device 132 may be used to determine a degree of doneness of the food or a degree to which the food is cooked. The degree to which the consumable item is cooked may alter the presence of nutrients, e.g., by degrading and/or converting nutrients as a result of applied heat. Therefore, in some embodiments, based on the consumable data 122 and the degree to which the consumable item is cooked, the nutrient scoring system 100 may determine a score 124 according to a quantity of various nutrients as described above. As a result, the nutrient scoring system 100 may output the score 124 based upon the microwave heating of the consumable item.

In another example, the smart device 130 may include, e.g., a smart scanner. The smart scanner may include computing resources such as the processor(s) 107 and storage device 101, the RAM 103, the output device interface 105 and the input device interface 109, among other computing resources, to score each consumable item. In some embodiments, some consumable items may include a label, such as a nutrition label, that include a machine-readable indicia encoding information regarding the consumable data 122, such as, e.g., nutrient quantities, item size and/or weight, or other suitable consumable data. Accordingly, in some embodiments, the user may input consumable data 122 including a type and/or name and/or category of the consumable item to the nutrient scoring system 100. In some embodiments, the user may input the consumable data 122 using, e.g., via the input device interface 109, the computing device 120, a keyboard, a touchscreen, one or more buttons or touch-sensitive switches, or other input device connected to the input device interface 109 or any combination thereof.

In some embodiments, the smart scanner may include a sensor device 132 including a scanner (e.g., an optical scanner or other scanner) for scanning the machine-readable indicia such as a barcode, a quick reference (QR code), or other machine-readable indicia. Accordingly, the user may then place the consumable item in a line of sight of the sensor device 132. The sensor device 132 may scan the machine-readable indicia and decode information encoded therein about the consumable item, such as, e.g., a serial number, a size, a weight, a name, a type, a category, a portion size, one or more nutrient quantities, etc. In some embodiments, the machine-readable indicia may include, e.g., an identifying marker, such as a serial number, brand and product name, or other identifier. The nutrient scoring system 100 may use the identifier to access in the content data 113 nutrition information associated with the consumable item. Therefore, in some embodiments, based on the consumable data 122 and the data decoded from the machine-readable indicia, the nutrient scoring system 100 may determine a score 124 according to a quantity of various nutrients as described above. As a result, the nutrient scoring system 100 may output the score 124 based upon scanning the consumable item.

Figure 2:
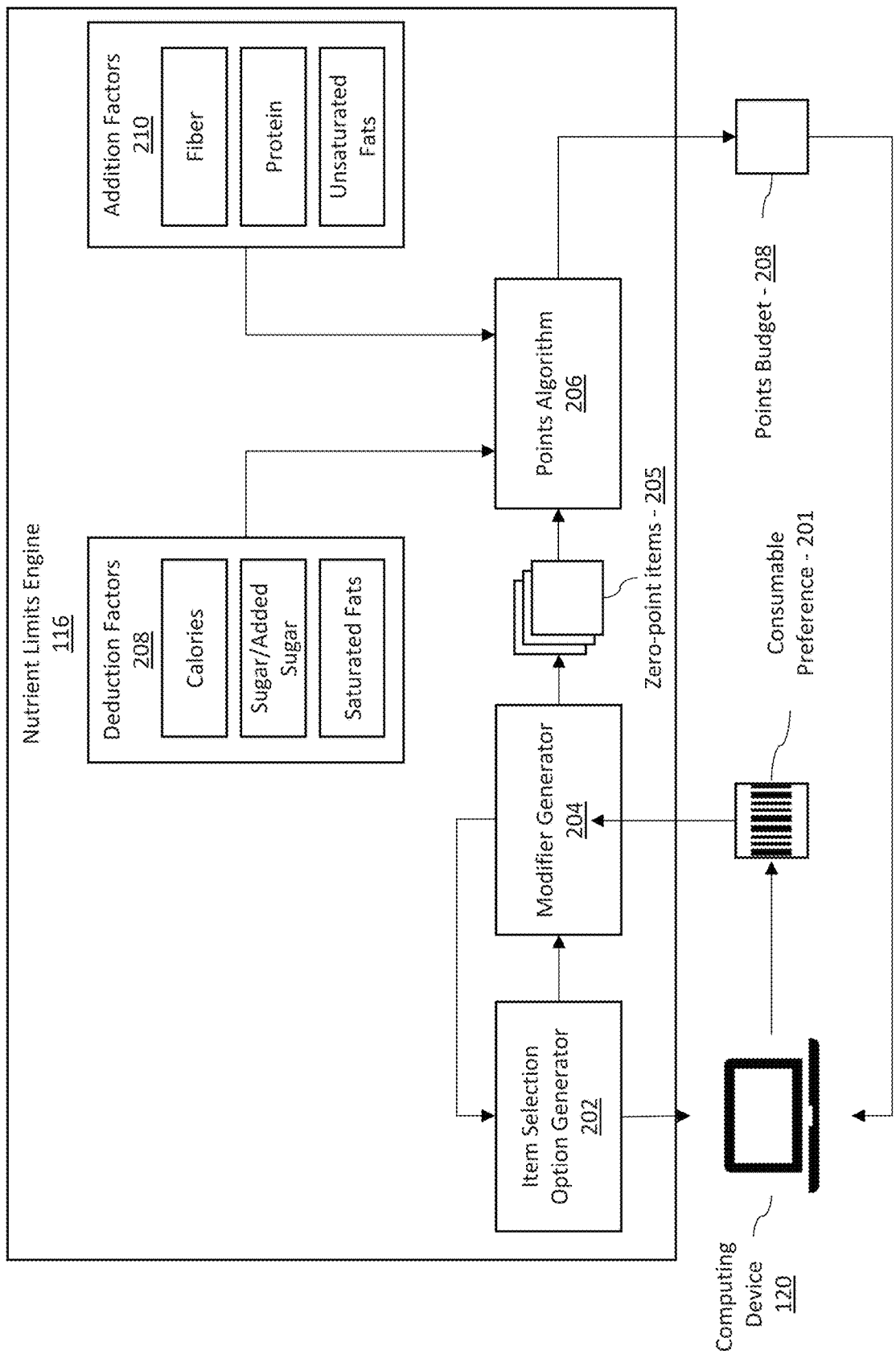
FIG. 2 is a block diagram of the nutrient limits engine 116 of the nutrient scoring system 100 in accordance with one or more embodiments of the present disclosure.

FIG. 2 is a block diagram of the nutrient limits engine 116 of the nutrient scoring system 100 in accordance with one or more embodiments of the present disclosure.

In some embodiments, in order to formulate a score budget and the zero scored consumable items, the nutrient limits engine 116 may employ a questionnaire presenting to the user on the computing device 120. In response to each question of the questionnaire, the user may select a consumable preference 201. In some embodiments, the goal of the questionnaire is to create a member's personalized zero scored consumables list of zero-value items 205 and score budget 208 based on their food preferences and ensure that their final score budget 208 is sufficient to fit in the foods with score values they also enjoy eating often.

In some embodiments, an item selection option generator 202 may generate a question of the questionnaire for user response. The question may be provided to the computing device 120 and displayed on a display thereof. The user may then select a response to the question to select a consumable preference 201 that defines a choice modifier. In some embodiments, the consumable preference 201 may be received by a modifier generator 204 that determines a subset of available questions that the item selection option generator 202 may provide to the user. For example, a consumable preference 201 that includes a particular consumable category or particular consumable item may result in the modifier generator 204 modifying the options for the next question in response to the particular consumable category or particular consumable item. Accordingly, the choice modifiers determine the logic driving the number of selection options and/or the content of the selection options presented by the item selection option generator 202. Each consumable preference may define the user's zero-value items 205 personalized to the user.

In some embodiments, each zero scored food category has a score value assigned to it that is deducted from the user's total score budget when selected in their questionnaire. In some embodiments, the score values in the below table are based on food frequency survey data (conducted in June 2020; n=227 current members) given the frequency and quantity eaten in a member's average day when that member has these consumable categories as zero scored items.

| Food Category | Score Value per Serving |
|---|---|
| Vegetables (non-starchy) | n/a |
| Fruits | 3 |
| Eggs | 2 |
| Non-fat yogurt & cottage cheese (plain, unsweetened) | 2 |
| Fish & shellfish | 1 |
| Chicken & turkey breast (skinless) | 1 |
| Beans, peas, lentils | 2 |
| Tofu & tempeh | 1 |
| Potatoes & sweet potatoes | 2 |
| Oatmeal | 2 |
| Brown rice & quinoa | 3 |
| Whole wheat pasta | 2 |
| Avocado | 3 |
| Corn & popcorn (plain, air-popped) | 1 |

In some embodiments, the consumable preferences 205 score budget will be calculated based on a member's age, biological sex, height, weight, and their zero scored categories. Personalized zero scored foods reflect each member's food preferences as indicated throughout the questionnaire.

In some embodiments, the zero scored items 205 are provided to a score algorithm 206 to determine the score budget 208. In some embodiments, the score algorithm 206 may determine the score budget based on deduction factors 308 and addition factors 310 modifying a base score budget associated with the user (e.g., see above for the daily and weekly score allowances). In some embodiments, deduction factors 308 reduce the score budget based on the quantity of calories, sugar, added sugar and/or saturated fats in the zero scored items 205. In some embodiments, the addition factors 310 increase the score budget based on a quantity of fiber, protein and/or unsaturated fats in the zero scored items 205. In some embodiments, the total value of each zero scored item may be determined based on a multiplier associated with each nutrient. An example of the multiplier values is set forth in the table below:

| Overview table: Algorithm multipliers per nutrient | | |
|---|---|---|
| Nutrient | | Multiplier |
| Calculated Calories | | 1.01 |
| Sat Fat | + | 9.7 |
| Natural Sugar | + | 0.9 |
| Added Sugar | + | 4.5 |
| Alcohol | + | 0.2 |
| Protein | − | 2.7 |
| Rewardable Fiber | − | 9.3 |
| Unsat Fat | − | 1.2 |

In some embodiments, based on the multipliers and nutrient quantities, metrics for a maximum score may be determined to indicate a daily intake score value associated with the user. These metrics may include, e.g., carbohydrates ("carbs") without fiber, calculated calories, unsaturated fat, natural sugar, rewardable fiber, etc. as shown in the table below:

| Calculated Metrics Used in the Maximum Score Calculation | | |
|---|---|---|
| Metric name | Calculation steps | Impacted markets |
| [Carbs_without_Fiber *(gm)] | =[Total labelled Carbs (gm)] − [Fiber (gm)] | [US] [CA] |
| *For ANZ, BE, BR, CH, DE, FR, NL, SE, UK: [labelled Total Carbs] = [Carbs_without_Fiber] | | |
| *For US, CA: the labelled Total Carbs include fiber − Carbs_without_Fiber is a calculated value | | |
| [Calculated Calories (cal)] | =[Total Fat (gm) *9] +[Protein (gm) *4] +[(Carbs_without_Fiber (gm) − Sugar Alcohol (gm)) *4] +[Sugar Alcohol (gm) *2.4] +[Fiber (gm) *2}] +[Alcohol (gm) *7] | ALL |
| This applies for oil markers, including ANZ where food labels use kJ instead of k cal as unit type for total energy | | |
| [Unsat Fat (gm)] | =[Total fat (gm)] − [Sat Fat (gm)) | ALL |
| [Natural Sugar (gm)] | =[Total Sugar (gm)] − [Added Sugar (gm)] | ALL |
| [Rewardable Fiber** (gm)] | Step 1: [Fiber (gm)]/[Calculated Calories] *100 Step 2: → if result of step 1 is 3: => [Fiber (gm)] → if result of step 1 is >3 => 3 * [Calculated Calories]/100 | ALL |
| **Rewardable Fiber MaxPoints Algorithm uses a max cop for fiber to avoid benefitting artificially added fiber/fiber-based fillers in processed foods Per 100 cals max 3 gm Fiber is rewardable | | |

In some embodiments, these metrics may then be employed to determine the maximum score of the users' score budget 208 using a maximum score calculation as depicted in the table below:

| | Maximum Score Calculation |
|---|---|
| Step 1: Calculation of Points Calorie Equivalent | ([Calculated Calories]*1.01 + [SatFat(gm)]*9.7 + [Natural Sugar(gm)]*0.9 + [Added Sugar(gm)]*4.5 + [Alcohol(gm)]*0.2 − [Protein(gm)]1*2.7 − [Rewardable Fiber(gm)]*9.3 − [Unsat Fat (gm)]*1.2) Weight (gm) per serving |
| Step 2: Calculation of decimal Points per Serving | $\dfrac{\text{Points Equivalent Calories ( = result step 1)}}{29 \text{ (new denominator)}} * \text{Serving Size}$ |
| Step 3: Rounding to whole number | Round decimal Points per serving(= result step 2) to the nearest whole number |

Figure 3:
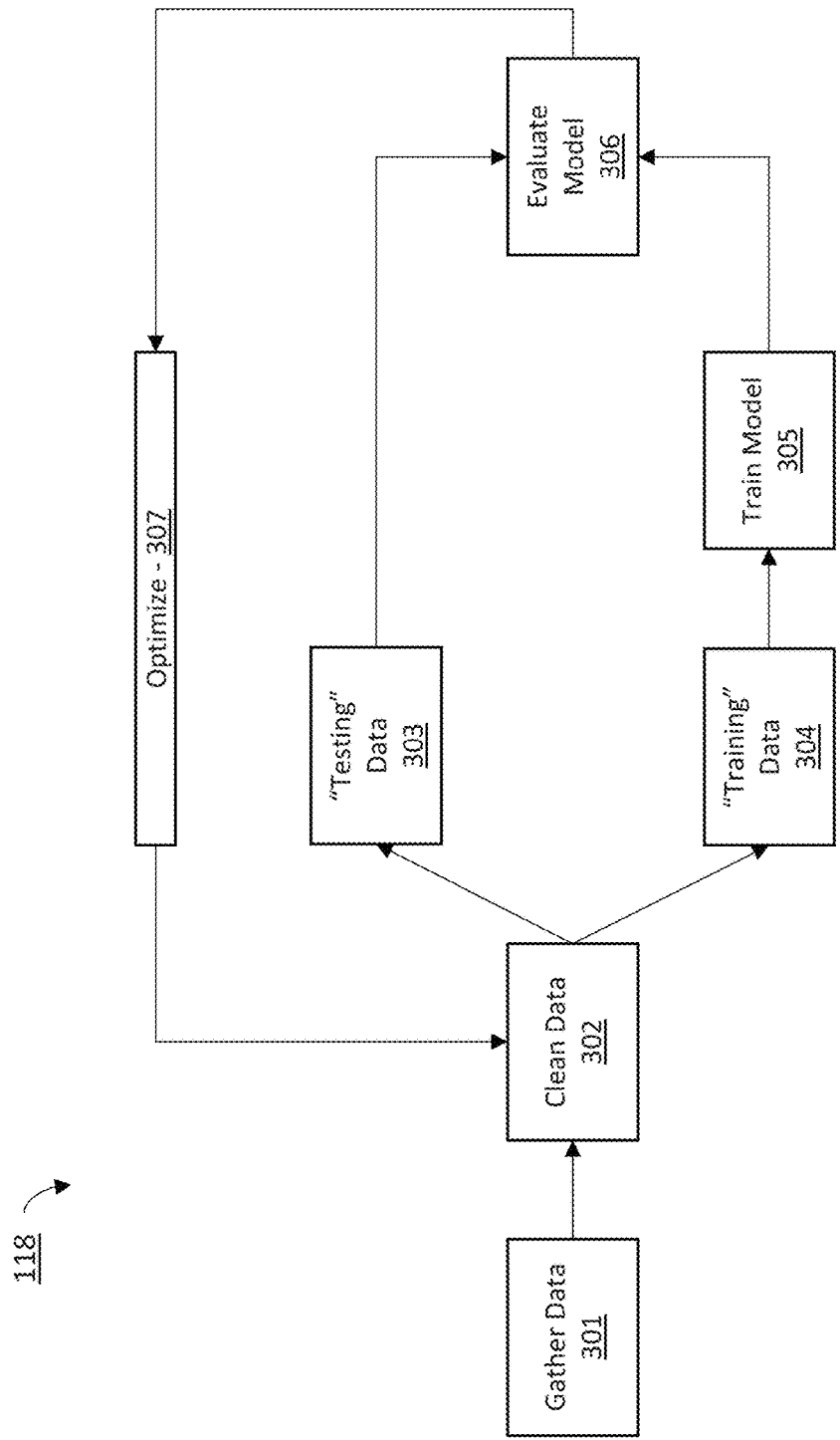
FIG. 3 illustrates a flowchart of an illustrative methodology for evaluating and optimizing the nutrient prediction model engine 117 of the nutrient scoring system 100 in accordance with one or more embodiments of the present disclosure.

FIG. 3 illustrates a flowchart of an illustrative methodology for evaluating and optimizing the nutrient prediction model engine 117 of the nutrient scoring system 100 in accordance with one or more embodiments of the present disclosure.

In some embodiments, the nutrient prediction model engine 117 may be used to train, evaluate and run a nutrient prediction model. In some embodiments, for training the nutrient prediction model, the nutrient prediction model engine 117 may be provided with data gathered at step 301. In some embodiments, the gathered data may include consumable data of known consumables with known nutrient contents. For example, the gathered data may include, e.g., nutrition data for 93,247 foods from a food database. Where available, added sugar information from the label was used (N=68,156), otherwise it was estimated by a team of registered dietitian nutritionists (N=25,091). In some embodiments, the food containing high amounts of added sugar, which are more likely to be ultra-processed foods, may have differing macro and micronutrient profiles, relative to whole and/or unprocessed foods. Therefore, added sugar values may be estimated from other nutritional information contained in the nutrition label, such as protein and fiber. Additionally, the relationship between added sugar and other nutrients to be nonlinear and contain interactions; therefore, a gradient boosted trees model may be used to predict added sugar values, which handles these conditions well. Similarly, other nutrients may have similar conditions, and may be used for training a model for prediction.

In some embodiments, the data may be cleansed at step 302 to remove invalid foods, such as, e.g., foods with unknown nutritional information, foods where the default portion size was less than 1 calorie to avoid errors due scaling (n=1852) or other errors.

In some embodiments, upon cleaning, the data may be separated into testing data 303 and training data 304. In order to evaluate the accuracy of the nutrient prediction model, an unbiased test sample may be generated by stratifying the available data on consumption frequency and randomly sampled 20% of the data to be held out of the model training process. The dataset also included category labels, which were used to perform an in-depth analysis of error rates on the main sources of added sugar as identified by the USDA. As all foods were scaled to 100 kcal for normalized reporting of results.

In some embodiments, the training data 304 is used to build the model and train the model at step 305. In some embodiments, the training data 304 may include, e.g., 80% of the data.

In some embodiments, nutrition information, such as, calories, grams of carbohydrates (without fiber or sugar alcohols), grams of total fat, grams of saturated fat, grams of sugar, grams of fiber, grams of protein and milligrams of sodium, or other nutrient information or any combination thereof in a single serving may be used as features to predict the value of added sugar in each serving. In some embodiments, 4-fold cross-validation may be employed within the training dataset, and a grid search performed over maximum tree depth (5, 10 or 20), learning rate (0.1 or 0.01), minimum child weight (3, 5, or 8), the subsample ratio of columns when constructing each tree (0.75, 0.9 or 1), subsample ratio of the training data (0.5, 0.75 or 0.9), and the number of trees (1000, 2000, 3000 or 4000) to determine the optimal set of hyperparameters.

In some embodiments, upon training, the model is evaluated at step 306 using the testing data 303 and the 4-fold cross-validation described above.

In some embodiments, based on the evaluation, the model may be optimized at step 307, e.g., using suitable backpropagation and/or gradient descent or other optimization algorithms. Subsequently, the optimized model was used to predict the added sugar values in the test data.

In some embodiments, the 1 model may be optimized for nutrient relationships, by utilizing SHAP (SHapley Additive exPlanations) values to evaluate the importance of each feature (e.g., nutrient) and its relationship to other features (e.g., nutrients).

In an example test of a nutrient prediction model engine 117, added sugar values averaged 1.92 g (SD=8.53; information from label: M=1.05, SD=3.62; registered dietitian nutritionist estimated: M=4.27, SD=15.08) per serving, and 1.50 g (SD=38.56; information from label: M=1.34, SD=45.02; registered dietitian nutritionist estimated: M=1.94, SD=4.56) per 100 kcal portion.

The results of the grid search indicated that a model trained with a maximum tree depth of 10, a learning rate of 0.01, a minimum child weight of 5, a subsample ratio of columns of 0.9, a subsample ratio of rows of 0.5 and 3000 trees performs best to predict the added sugar values of foods. Using these hyperparameters a gradient boosted tree model may be trained on the training data and predicted added sugar values in the test dataset.

Figure 11:
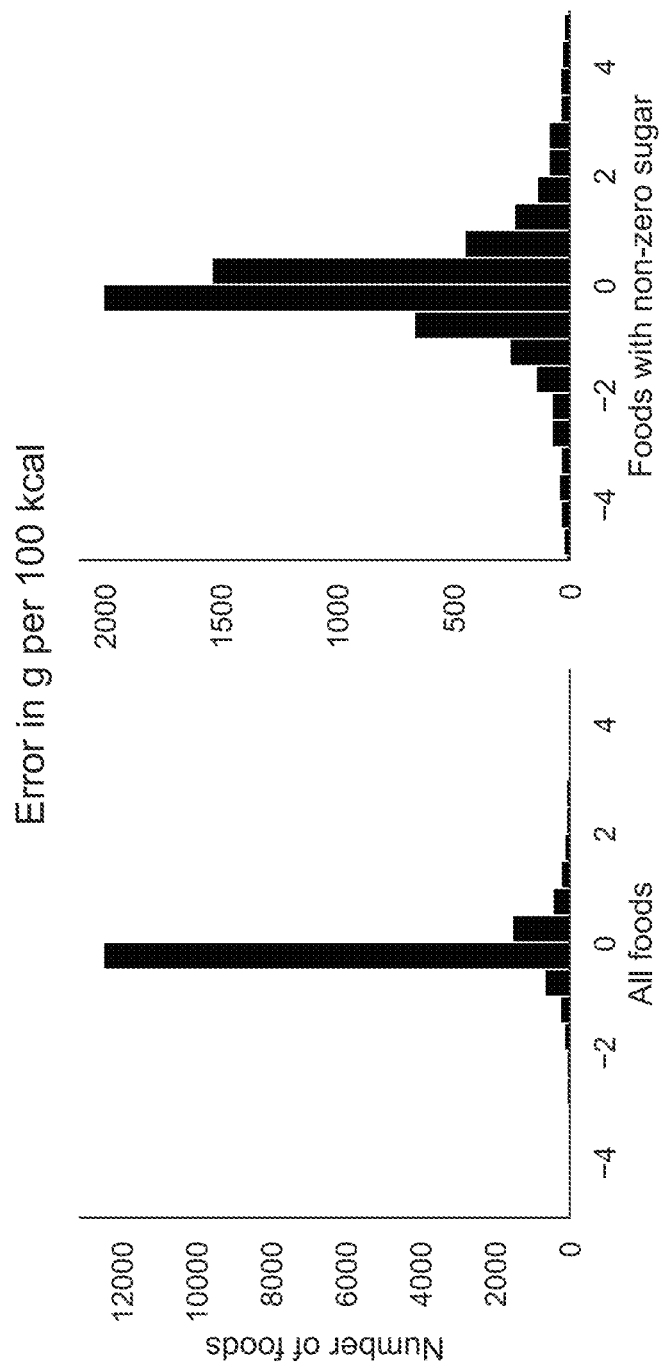
FIG. 11 depicts error in a prediction of added sugar values in g per 100 kcal using the nutrient prediction model engine 117 of the nutrient scoring system 100 in accordance with embodiments of the present disclosure.

Evaluation of the final model in the example test based on the test data 303 showed that the model was able to explain 94.2% of the variance in the dependent variable, which was added sugar. The mean added sugar value in the test dataset was 2.2 g (SD=10.0) per serving and mean added sugar per 100 kcal was 1.4 g (SD=3.8), and the mean absolute error of the estimation was 0.5 g per serving and 0.4 g/1.6 kcal per 100 kcal. If only predicting foods with non-zero sugar content in the model, 93.8% of the variance was explained. In this subset of the test data, the mean added sugar was 5.7 g (SD=15.7) per serving and 3.6 g per 100 kcal (SD=5.5), and the mean absolute error of the estimation was 1.32 g per serving (1.1 g/4.4 kcal per 100 kcal). FIG. 11 shows error in grams per 100 kcal for all foods and for foods with non-zero sugar content. The errors are roughly symmetrically distributed around zero with a slight bias towards overestimating added sugar content.

Figure 12:
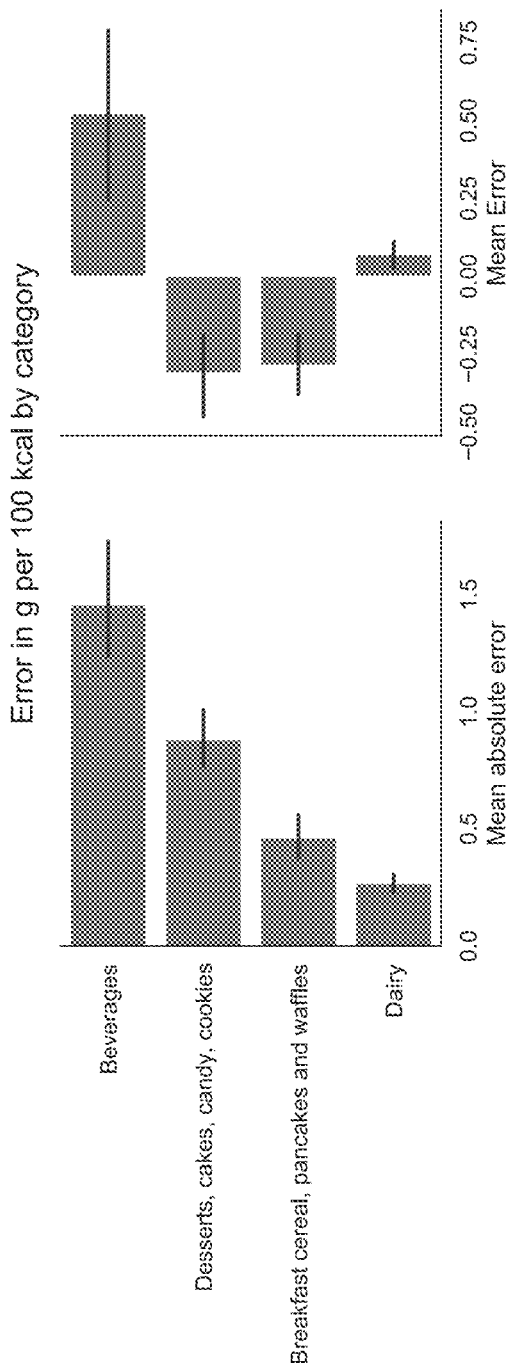
FIG. 12 depicts mean absolute and mean error in the prediction of added sugar values in g per 100 kcal in categories high in sugar content using the nutrient prediction model engine 117 of the nutrient scoring system 100 in accordance with embodiments of the present disclosure.

Category labels in the dataset that overlap with main sources of added sugar as identified by the USDA include "Beverages", "Desserts, cakes, candy, cookies", "Breakfast cereal, pancakes and waffles", and "Dairy". FIG. 12 shows that the mean absolute error per 100 kcal is largest in the "Beverages" category, with an error of 1.5 g (6 kcal) per 100 kcal. Closer examination of the error shows that added sugar content in beverages is often overestimated, which can happen in beverages such as fruit juices, which are high in naturally occurring sugar.

In some embodiments, the feature importance may be investigated using Shapley Additive Explanations (SHAP) values or other suitable "explainable AI" technique or any combination thereof. In some embodiments, SHAP values refer to a game theoretic approach to explain the output of any machine learning model by connecting optimal credit allocation with local explanations using the classic Shapley values from game theory and related extensions. In some embodiments, SHAP values may be used to indicate that the value of sugar was the most important predictor for estimating added sugar content of a food (see FIG. 13). As shown in FIG. 14A the predicted value of added sugar linearly depends on the sugar content of a food. However, other features also influence the prediction. As FIG. 14B shows, for high values of sugar, the protein content of a food modulates the prediction. In that case, lower protein content indicates higher added sugar content. FIG. 14C shows that lower fiber content also leads to higher predictions of added sugar, especially if sugar content is high.

In some embodiments, a gradient boosted tree model of a nutrient prediction model may be trained to predict the added sugar content of foods. In some embodiments the achievable prediction accuracy allows for making clinically important predictions that can inform consumer behavior. For example, where nutrition data for 93,247 foods is utilized, with added sugar values averaging 1.92 grams per serving and 1.5 grams per 100 kcal portion, the resulting model may explain over 93% of the variation in added sugar in both the model with all foods included and the model predicting only foods with non-zero sugar content, suggesting a highly accurate model errors for added sugar were either zero or very low for both foods with non-zero sugar (mean absolute error=1.6 kcal per 100 kcal), as well as for all foods (mean absolute error=4.4 kcal per 100 kcal). For those foods where error may be observed, there is a slight bias towards overestimating added sugar, which allows for conservative estimation. Given consumers tend to underestimate the calorie and nutrient content of foods and that average daily added sugar consumption is above recommended thresholds, slight overestimation of sugar in the model is preferred relative to underestimation. Among the highest sources of added sugar consumption by Americans, which include beverages, desserts, cakes, candy, cookies, breakfast cereal, pancakes, waffles, and dairy, we see the highest errors for estimation of added sugar content for beverages. These errors appear to stem primarily from overestimating added sugar content within fruit juices, which are high in naturally occurring sugar. This is consistent with what was observed within the model, as the value of total sugar is the strongest predictor for estimating added sugar content of a food. Specifically, the predicted value of added sugar is linear with the total sugar content of the food. Additional predictors for higher added sugar content include low protein content in the food, as well as a low fiber content, particularly when paralleled with higher total sugar content.

Excess consumption of added sugar can contribute toward poor nutrition and a dietary pattern that can increase risk for obesity, diabetes, and cardiovascular disease in adults and in children as young as seven years old. Currently, average added sugar consumption is higher than the recommended intake of less than ten percent of daily calories. Given that only the U.S. and Canada are the only countries to date to include added sugar in the Nutrition Facts label, most of the world's population does not have access to added sugar information. As recent data suggest that detailed information about the nutrition content of foods is efficient in guiding consumption behaviors, the data presented herein is important as it can be used to estimate added sugar of a food from the information provided within a traditional Nutrition Facts label, including calories, milligrams of sodium, and grams of carbohydrates, total fat, saturated fat, sugar, fiber, and protein. This demonstrates an opportunity to develop digital solutions, such as a website that estimates the added sugar content of foods, or an app that allows to scan the traditional nutrition label of food items, and then shares the estimated added sugar content of the item to inform healthy decision making. In the absence of such tools, consumers are left to determine the healthfulness of a food by estimation alone or by nutrition claims on the packaging of the food. However, a systematic review investigating the impact of nutrition claims related to sugar content on food choices and energy intake suggests that health-conscious consumers perceive 'reduced-sugar' foods to be healthier than 'regular' foods.

In some embodiments, Xgboost may be used to build a gradient boosted tree model that ensures that the resulting model is scalable and portable between platforms, making it an optimal candidate to serve predictions in digital applications. While the added sugar content in foods is mainly a linear function of sugar content, there is additional information that can be gained from considering the values of other nutrients, such as protein or fiber. Gradient boosted tree models are well suited to pick up such additional information as they optimize predictions by adding trees such that errors in predictions from previous trees are minimized. While tree-based methods can be susceptible to overfitting, i.e. matching the characteristics of the training data so well that the resulting model fails to generalize to new data. Here this risk was mitigated by using cross-validation within the training data to determine the best set of hyperparameters, which either introduce subsampling of the training data or limit the allowed complexity of the final model, to minimize overfitting. All results are reported on a held-out test dataset which was not used during training, so reported results reflect the performance of the model on new data, as would be encountered when applying the model to predict the added sugar content of new foods in an online application.

Therefore, in some embodiments a gradient boosted tree model may be trained to accurately predict the added sugar content of foods, utilizing information found on a traditional Nutrition Facts label. This will allow for consumer-friendly, digital, and saleable apps to be developed to help inform consumers about added sugars in the foods they wish to consume, even in countries across the globe that do not provide added sugar information in the Nutritional Facts label.

Figure 4:
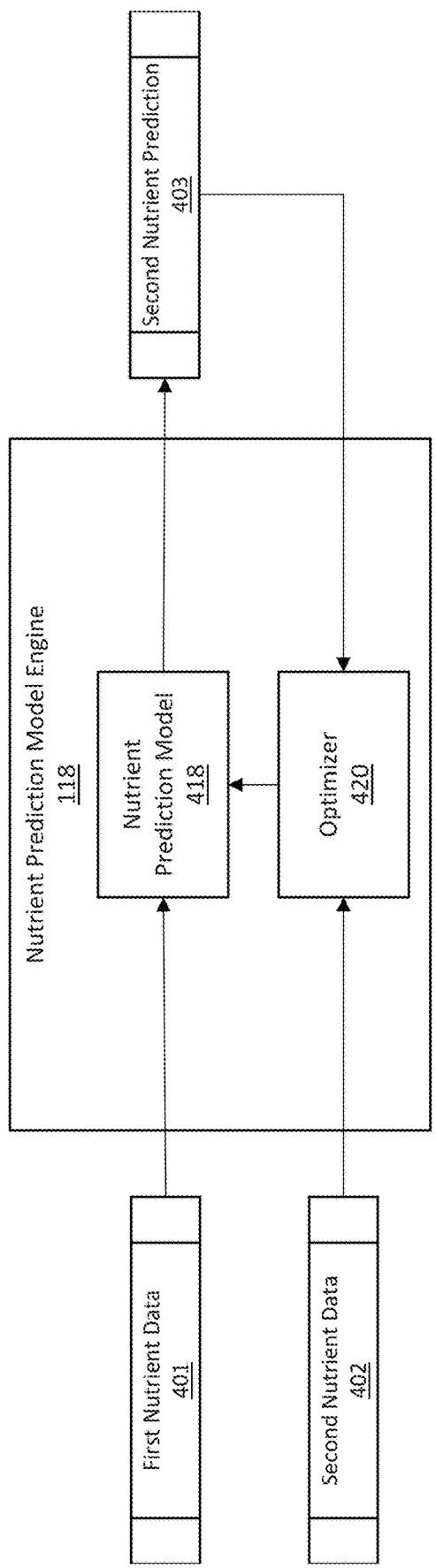
FIG. 4 is a block diagram of the nutrient prediction model engine 117 of the nutrient scoring system 100 in accordance with one or more embodiments of the present disclosure.

FIG. 4 is a block diagram of the nutrient prediction model engine 117 of the nutrient scoring system 100 in accordance with one or more embodiments of the present disclosure.

In some embodiments, the nutrient prediction model engine 117 may utilize the nutrient prediction model 418 to predict a second nutrient prediction 403 based on the first nutrient data 401 of a consumable item.

In some embodiments, the nutrient prediction model 418 ingests the first nutrient data 401 and produces a prediction of a second nutrient prediction 403 for each first nutrient data 401. In some embodiments, to produce this prediction, the nutrient prediction model 418 may include a machine learning model including a classification model, such as, e.g., a recurrent neural network (RNN), decision trees, random forest, support vector machine (SVM), or any other suitable algorithm for a nonlinear regression model. In some embodiments, for computational efficiency while preserving accuracy of predictions, the nutrient prediction model 418 may advantageously include a decision tree model.

Accordingly, the nutrient prediction model 418 ingests a first nutrient data 401 and processes the attributes encoded therein using the model to produce a model output vector. In some embodiments, the model output vector may be decoded to generate a value including the second nutrient prediction 403 that represents a quantity of the nutrient in the consumable item.

In some embodiments, second nutrient data 402 may be provided to the nutrient prediction model engine 117. The second nutrient data 402 may include a known value of the nutrient for the consumable item. Thus, the second nutrient prediction 403 may be compared against the second nutrient data 402 to determine an error of the nutrient prediction model 418. Based on the difference between the second nutrient prediction 403 and the second nutrient data 402, the parameters of the nutrient prediction model 418 may be updated to improve the accuracy of the recurring data entry classification.

In some embodiments, training is performed using the optimizer 410. In some embodiments, the second nutrient prediction 403 fed back to the optimizer 410. The optimizer 410 may also ingest the second nutrient data 402. In some embodiments, the optimizer 410 may employ a loss function, such as, e.g., Hinge Loss, Multi-class SVM Loss, Cross Entropy Loss, Negative Log Likelihood, or other suitable classification loss function. The loss function determines an error based on the second nutrient data 402 and the second nutrient prediction 403. In some embodiments, the optimizer 410 may, e.g., backpropagate the error to the nutrient prediction model 418 to update the parameters using, e.g., gradient descent, heuristic, convergence or other optimization techniques and combinations thereof.

In some embodiments, the optimizer 410 may construct particular trained machine learning model by stacking multiple trees. Each decision tree, built via the above process, is prone to over-specification, where it too closely matches the underlying training data. In this case the model will not generalize effectively for un-seen data score during inference. In some embodiments, to avoid this, the stacking of multiple trees can be used. In some embodiments, the stacking can occur in two ways, the first way a so called "random forest" is created where the optimizer 410 constructs each tree using a random subset of available consumable data 122 and/or content data 113. The predictions from each resulting tree leaf are averaged for an inference result, e.g., a nutrient quantity. In some embodiments, in the second way, so called gradient-boosted trees, the optimizer 410 builds trees sequentially, where each subsequent tree has a target nutritional value which represents the difference between the true-result and the result that was predicted by the previous tree. In this way, gradient-boosted trees are iteratively focusing on reducing the predictions which have the largest error toward ground truth.

In some embodiments, to create the trees of the nutrient prediction machine learning model, the optimizer 410 may be used to train a decision tree model via branching based on known pairings of listed nutrients quantities and unlisted nutrient quantities. The branching is part of the decision tree building process, which is the training process. The inference process simply takes input nutrient data and follows each branch of the tree toward each tree's terminal node. Each terminal node represents some contribution to the final prediction which is the output of the model.

In some embodiments, the optimizer 410 may create the decision trees during training using a greedy optimization process. The training process encompasses the branching process, but it also includes a pruning process.

In some embodiments, the branching process has several parts to it, firstly, one of the feature-dimensions (in our case, one of the existing, known nutrient values) is chosen to create a branch. This selection process varies according to the model's parameterization. It could come from a random subset of all possible nutrient values, or it could be selected from all possible nutrient values. The selection can also be based on the optimality of the performance for a branch based on each individual nutrient value.

In some embodiments, branch splitting criteria and performance is based on choosing a threshold within a single nutrient value. In some embodiments, the branch will then split all of the predicted target nutrients to be less than, or greater than or equal to, the threshold. In this case, all target nutrient values on either side of the threshold are aggregated into an average, which represents the decision tree predicted nutrient value for that "leaf" resulting from the threshold choice. The threshold is iteratively evaluated to find the optimal location, which produces the lowest mean-squared error between predictions resulting from the split choice on each particular branching variable.

In some embodiments, this branching process will be repeatedly applied, adding more leaves, and thereby creating more aggregated predicted values for the target nutrient across each leaf. The process stops when a predefined target criteria is met, such as a limiting depth, or a minimum number of existing target nutrient data score to aggregate within the potential leaf.

In some embodiments, after branching, during training the optimizer 410 may performed a "pruning" operation. While branching occurs by building a tree from the top-down, pruning works from a bottom up traversal. Each node is visited upwards after building to determine if removing or pruning the branch would ultimately create a lower mean-squared error in the totality of the resulting leaves. This controls the complexity of the decision tree being built.

In some embodiments, the optimizer 410 may therefore train the parameters of the nutrient prediction model 418 to approximate user behaviors in disputing data entries as duplicative based on feedback including the second nutrient data 402. As a result, the nutrient prediction model 418 may be continually trained and optimized based on user feedback.

Figure 5:
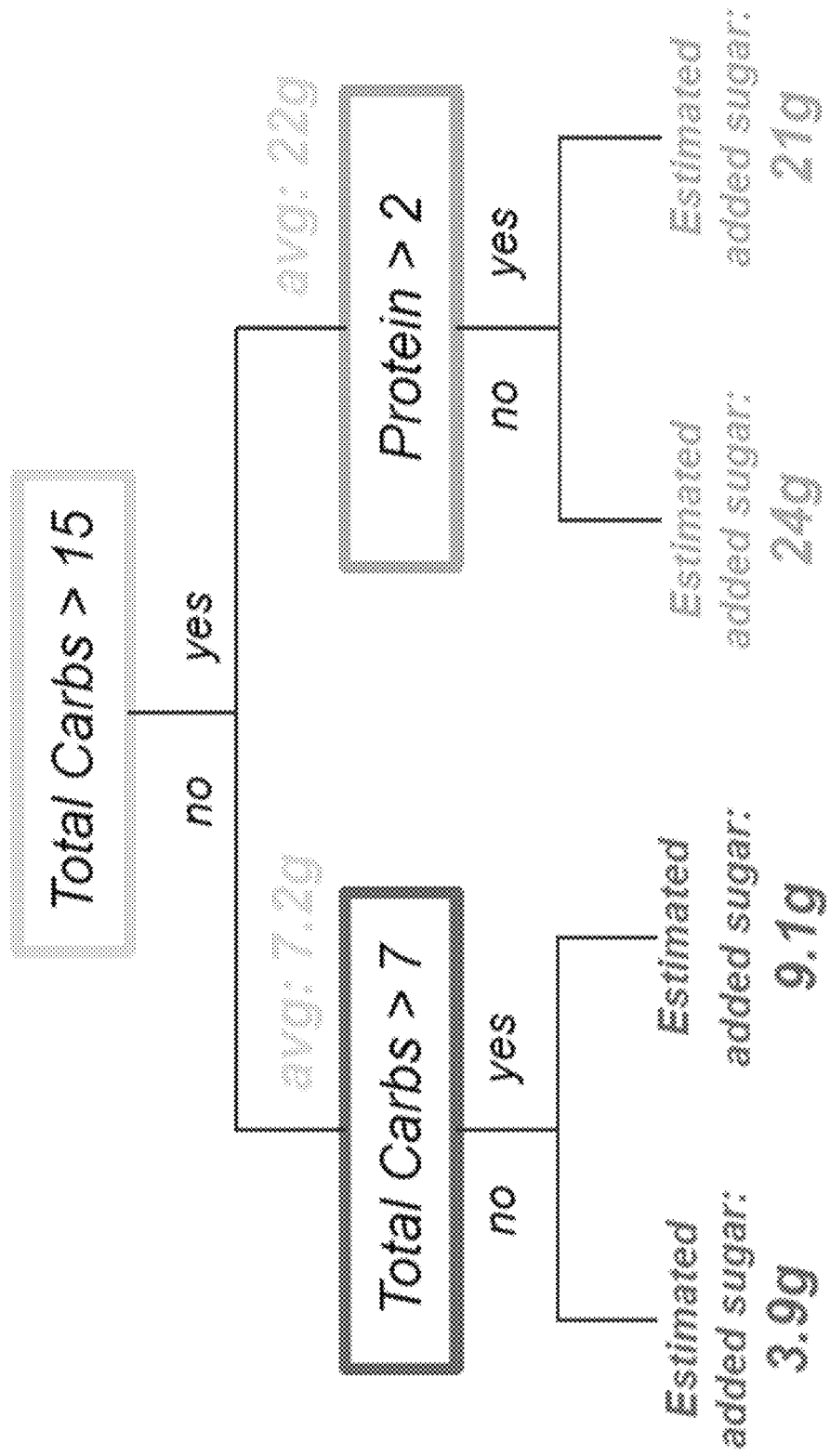
FIG. 5 illustrates an example decision tree for a nutrient prediction model of the nutrient prediction model engine 117 in accordance with one or more embodiments of the present disclosure.

FIG. 5 illustrates an example decision tree for a nutrient prediction model of the nutrient prediction model engine 117 in accordance with one or more embodiments of the present disclosure.

Figure 6:
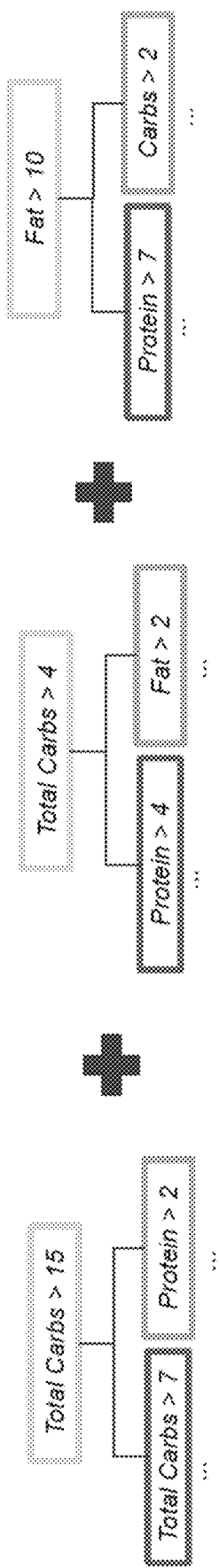
FIG. 6 illustrates an example set of decision trees for a nutrient prediction model of the nutrient prediction model engine 117 in accordance with one or more embodiments of the present disclosure.

FIG. 6 illustrates an example set of decision trees for a nutrient prediction model of the nutrient prediction model engine 117 in accordance with one or more embodiments of the present disclosure.

Figure 7:
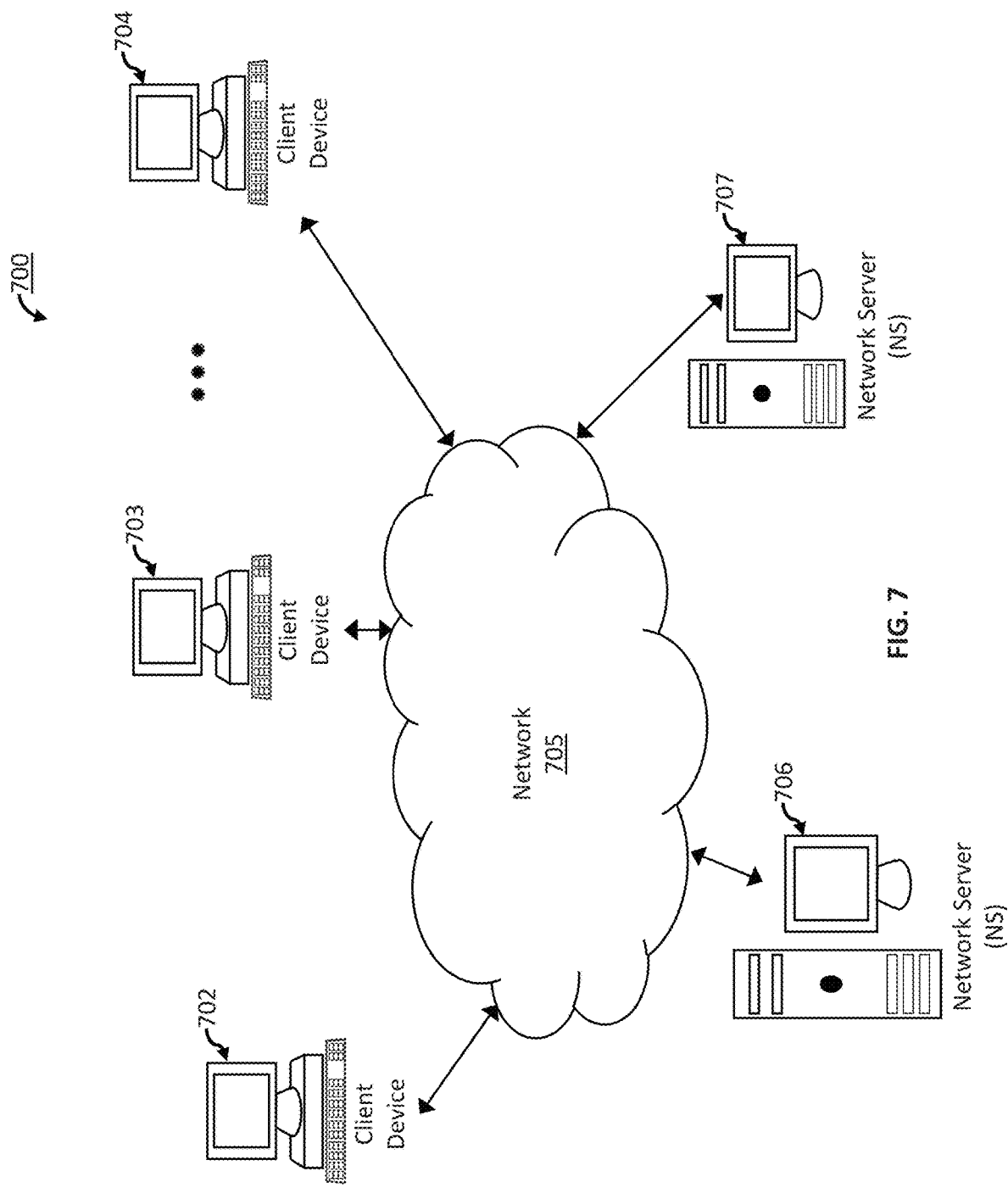
FIG. 7 depicts a block diagram of an exemplary computer-based system and platform 800 for the nutrient scoring system 100 in accordance with one or more embodiments of the present disclosure.
Figure 8:
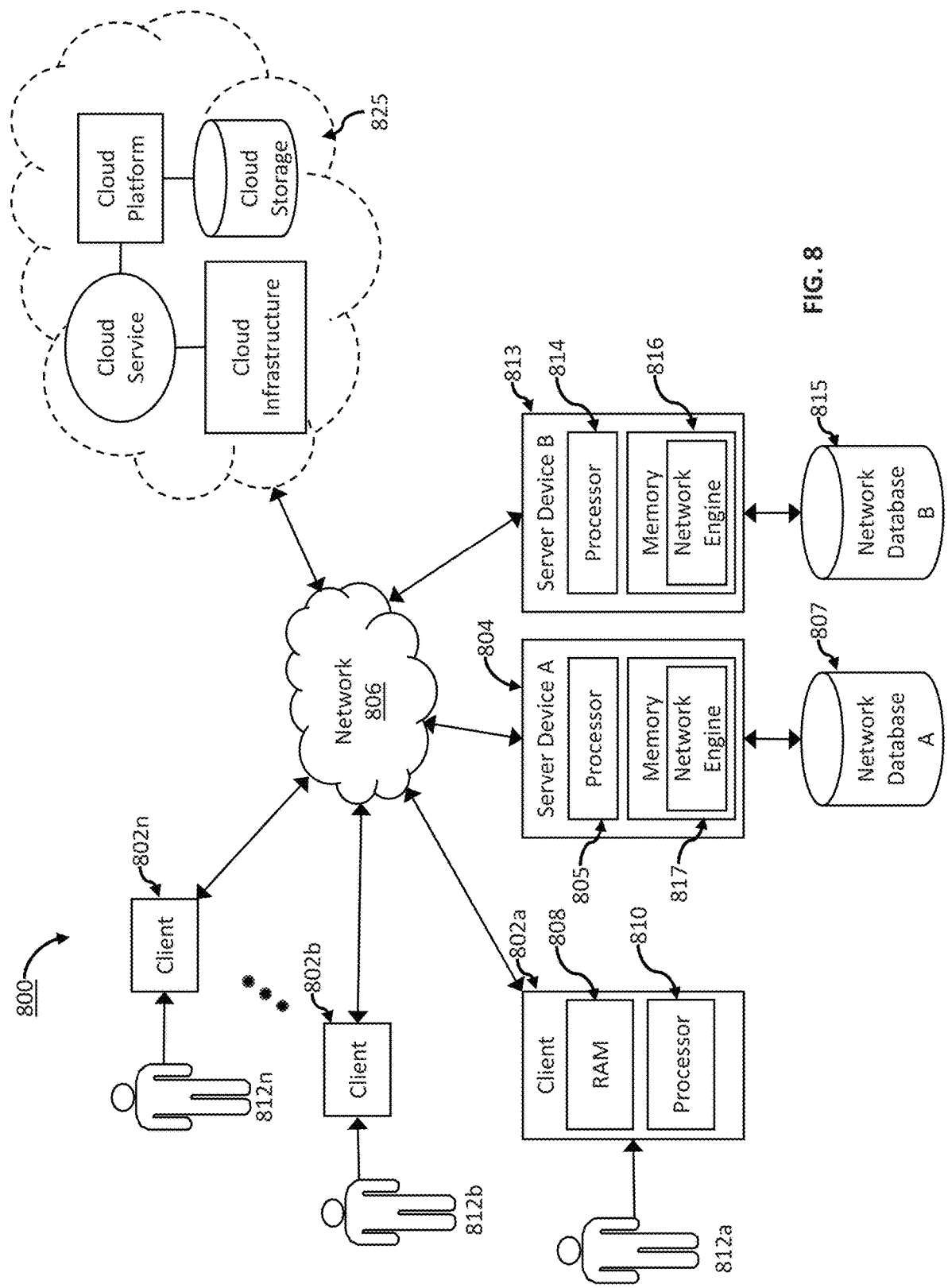
FIG. 8 depicts a block diagram of another exemplary computer-based system and platform 900 for the nutrient scoring system 100 in accordance with one or more embodiments of the present disclosure.

FIG. 7 depicts a block diagram of an exemplary computer-based system and platform 700 for the nutrient scoring system 100 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 700 may be configured to manage a large number of members and concurrent transactions, as detailed herein. In some embodiments, the exemplary computer-based system and platform 700 may be based on a scalable computer and network architecture that incorporates various strategies for assessing the data, caching, searching, and/or database connection pooling. An example of the scalable architecture is an architecture that is capable of operating multiple servers.

In some embodiments, referring to FIG. 7, member computing device 702, member computing device 703 through member computing device 704 (e.g., clients) of the exemplary computer-based system and platform 700 may include virtually any computing device capable of receiving and sending a message over a network (e.g., cloud network), such as network 705, to and from another computing device, such as servers 706 and 707, each other, and the like. In some embodiments, the member devices 702-704 may be personal computers, multiprocessor systems, microprocessor-based or programmable consumer electronics, network PCs, and the like. In some embodiments, one or more member devices within member devices 702-704 may include computing devices that typically connect using a wireless communications medium such as cell phones, smart phones, pagers, walkie talkies, radio frequency (RF) devices, infrared (IR) devices, citizens band radio, integrated devices combining one or more of the preceding devices, or virtually any mobile computing device, and the like. In some embodiments, one or more member devices within member devices 702-704 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, OFDM, OFDMA, LTE, satellite, ZigBee, etc.). In some embodiments, one or more member devices within member devices 702-704 may include may run one or more applications, such as Internet browsers, mobile applications, voice calls, video games, videoconferencing, and email, among others. In some embodiments, one or more member devices within member devices 702-704 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 702-704 may be specifically programmed by either Java, .Net, QT, C, C++, Python, PHP and/or other suitable programming language. In some embodiments of the device software, device control may be distributed between multiple standalone applications. In some embodiments, software components/applications can be updated and redeployed remotely as individual units or as a full software suite. In some embodiments, a member device may periodically report status or send alerts over text or email. In some embodiments, a member device may contain a data recorder which is remotely downloadable by the user using network protocols such as FTP, SSH, or other file transfer mechanisms. In some embodiments, a member device may provide several levels of user interface, for example, advanced user, standard user. In some embodiments, one or more member devices within member devices 702-704 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 705 may provide network access, data transport and/or other services to any computing device coupled to it. In some embodiments, the exemplary network 705 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 705 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 705 may include and implement, as an alternative or in conjunction with one or more of the above, a WiMAX architecture defined by the WiMAX forum. In some embodiments and, optionally, in combination of any embodiment described above or below, the exemplary network 705 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 705 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, OFDM, OFDMA, LTE, satellite and any combination thereof. In some embodiments, the exemplary network 705 may also include mass storage, such as network attached storage (NAS), a storage area network (SAN), a content delivery network (CDN) or other forms of computer or machine readable media.

In some embodiments, the exemplary server 706 or the exemplary server 707 may be a web server (or a series of servers) running a network operating system, examples of which may include but are not limited to Apache on Linux or Microsoft IIS (Internet Information Services). In some embodiments, the exemplary server 706 or the exemplary server 707 may be used for and/or provide cloud and/or network computing. Although not shown in FIG. 7, in some embodiments, the exemplary server 706 or the exemplary server 707 may have connections to external systems like email, SMS messaging, text messaging, ad content providers, etc. Any of the features of the exemplary server 706 may be also implemented in the exemplary server 707 and vice versa.

In some embodiments, one or more of the exemplary servers 706 and 707 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers, advertisement providing servers, financial/banking-related services servers, travel services servers, or any similarly suitable service-base servers for users of the member computing devices 701-704.

In some embodiments and, optionally, in combination of any embodiment described above or below, for example, one or more exemplary computing member devices 702-704, the exemplary server 706, and/or the exemplary server 707 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof.

FIG. 7 depicts a block diagram of another exemplary computer-based system and platform 800 for the nutrient scoring system 100 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing device 802*a*, member computing device 802*b* through member computing device 802*n* shown each at least includes a computer-readable medium, such as a random-access memory (RAM) 808 coupled to a processor 810 or FLASH memory. In some embodiments, the processor 810 may execute computer-executable program instructions stored in memory 808. In some embodiments, the processor 810 may include a microprocessor, an ASIC, and/or a state machine. In some embodiments, the processor 810 may include, or may be in communication with, media, for example computer-readable media, which stores instructions that, when executed by the processor 810, may cause the processor 810 to perform one or more steps described herein. In some embodiments, examples of computer-readable media may include, but are not limited to, an electronic, optical, magnetic, or other storage or transmission device capable of providing a processor, such as the processor 810 of client 802*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 802*a* through 802*n* may also comprise a number of external or internal devices such as a mouse, a CD-ROM, DVD, a physical or virtual keyboard, a display, or other input or output devices. In some embodiments, examples of member computing devices 802*a* through 802*n* (e.g., clients) may be any type of processor-based platforms that are connected to a network 806 such as, without limitation, personal computers, digital assistants, personal digital assistants, smart phones, pagers, digital tablets, laptop computers, Internet appliances, and other processor-based devices. In some embodiments, member computing devices 802*a* through 802*n* may be specifically programmed with one or more application programs in accordance with one or more principles/methodologies detailed herein. In some embodiments, member computing devices 802*a* through 802*n* may operate on any operating system capable of supporting a browser or browser-enabled application, such as Microsoft™, Windows™, and/or Linux. In some embodiments, member computing devices 802*a* through 802*n* shown may include, for example, personal computers executing a browser application such as Microsoft Corporation's Internet Explorer™, Apple Computer, Inc.'s Safari™, Mozilla Firefox, and/or Opera. In some embodiments, through the member computing client devices 802*a* through 802*n*, user 812*a*, user 812*b* through user 812*n*, may communicate over the exemplary network 806 with each other and/or with other systems and/or devices coupled to the network 806. As shown in FIG. 7, exemplary server devices 804 and 813 may include processor 805 and processor 814, respectively, as well as memory 817 and memory 816, respectively. In some embodiments, the server devices 804 and 813 may be also coupled to the network 806. In some embodiments, one or more member computing devices 802*a* through 802*n* may be mobile clients.

In some embodiments, at least one database of exemplary databases 807 and 815 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 9:
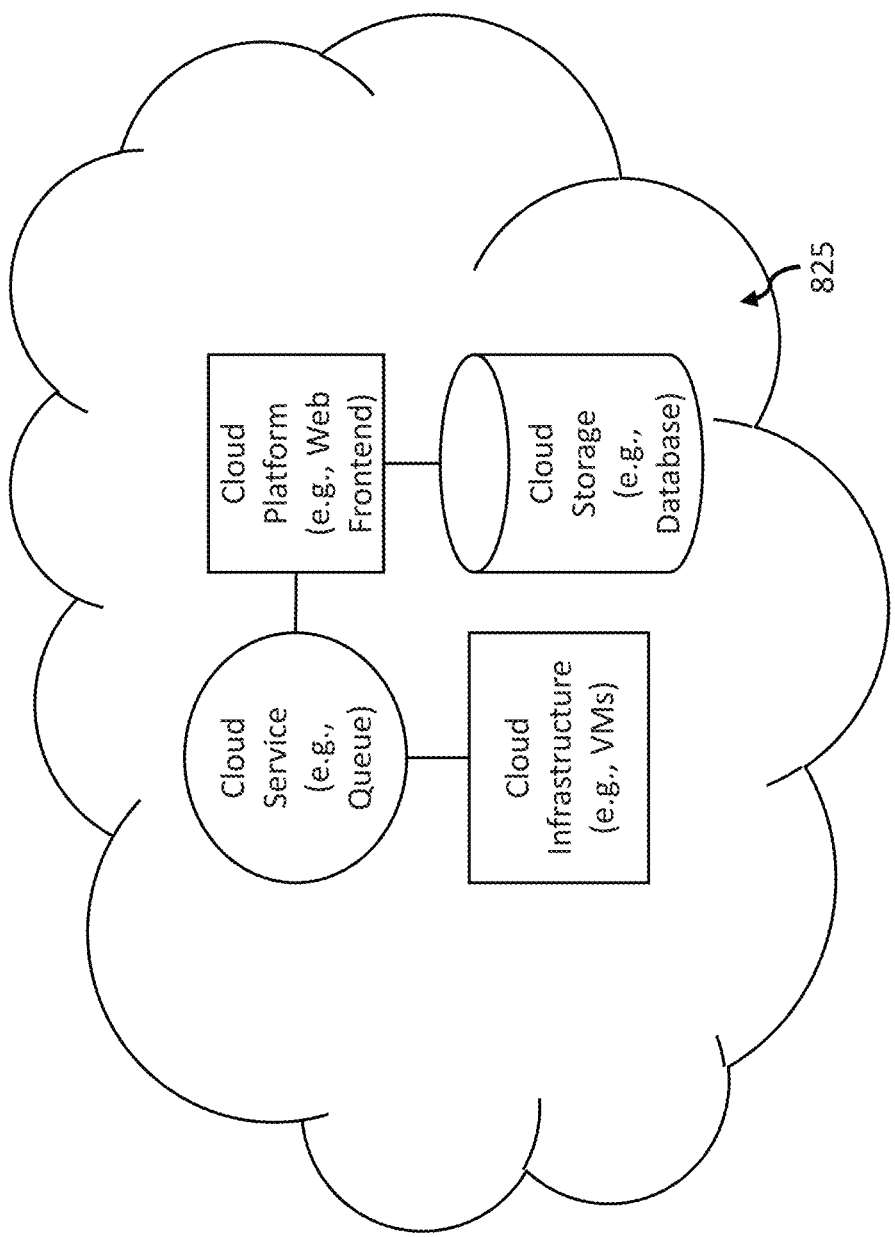
FIG. 9 illustrates schematics of an exemplary implementation of the cloud computing/architecture(s) in which the nutrient scoring system 100 of the present disclosure may be specifically configured to operate.
Figure 10:
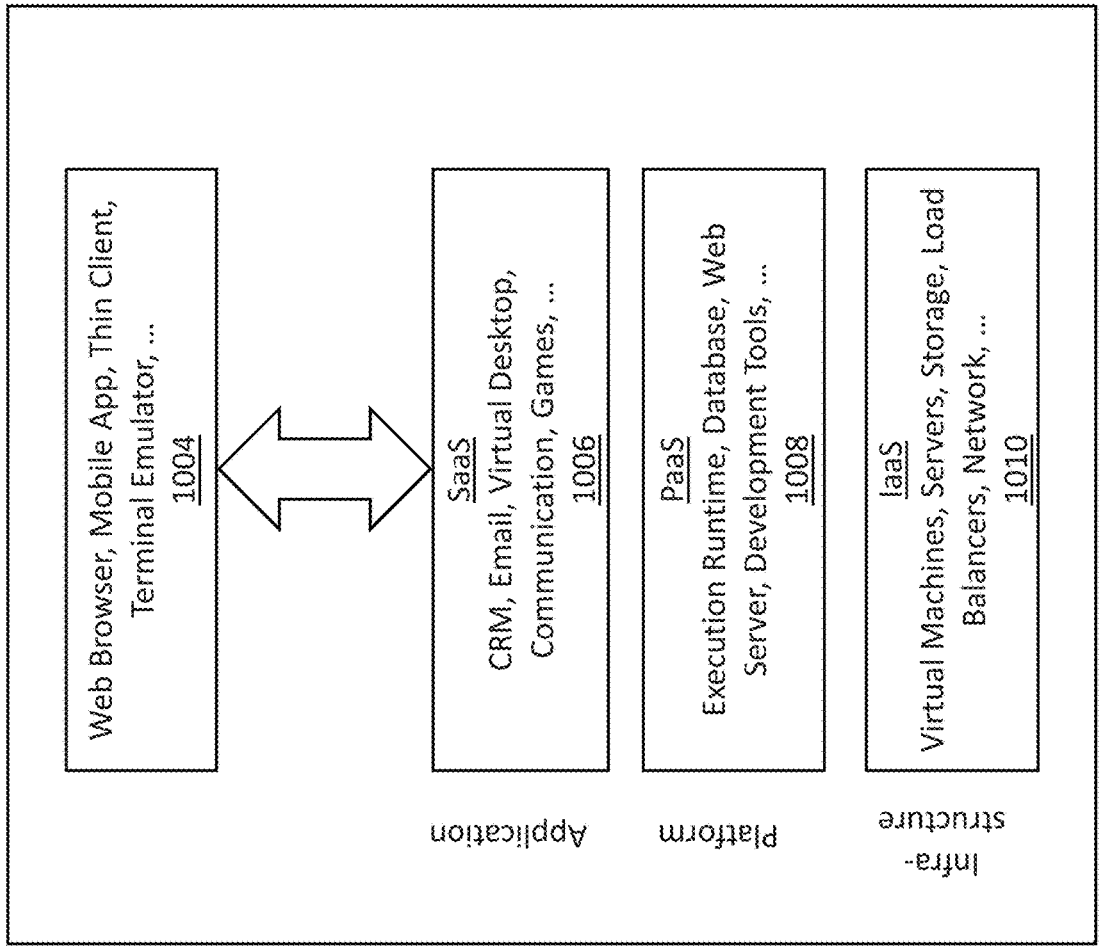
FIG. 10 illustrates schematics of an exemplary implementation of the cloud computing/architecture(s) in which the nutrient scoring system 100 of the present disclosure may be specifically configured to operate.

In some embodiments, the exemplary inventive computer-based systems/platforms, the exemplary inventive computer-based devices, and/or the exemplary inventive computer-based components of the present disclosure may be specifically configured to operate in a cloud computing/architecture 825 such as, but not limiting to: infrastructure a service (IaaS) 1010, platform as a service (PaaS) 1008, and/or software as a service (SaaS) 1006 using a web browser, mobile app, thin client, terminal emulator or other endpoint 1004. FIGS. 9 and 10 illustrate schematics of exemplary implementations of the cloud computing/architecture(s) in which the nutrient scoring system 100 of the present disclosure may be specifically configured to operate. FIG. 11 depicts error in a prediction of added sugar values in g per 100 kcal using the nutrient prediction model engine 117 of the nutrient scoring system 100 in accordance with embodiments of the present disclosure. Both for all foods and foods with non-zero sugar content the errors are roughly symmetrically distributed around 0 with a slight bias towards overestimating added sugar content. The mean absolute error was 0.4 g per 100 kcal for all foods, and 1.1 g per 100 kcal for foods with non-zero sugar content.

FIG. 12 depicts mean absolute and mean error in the prediction of added sugar values in g per 100 kcal in categories high in sugar content using the nutrient prediction model engine 117 of the nutrient scoring system 100 in accordance with embodiments of the present disclosure. As shown, the mean absolute error for beverages is 1.5 g (6 kcal) per 100 kcal. Examining the mean error shows that added sugar content in beverages is mostly overestimated, e.g. in fruit juices which are high in natural sugar but low in added sugar, which is expected to lead to more conservative consumption behaviors.

Figure 13:
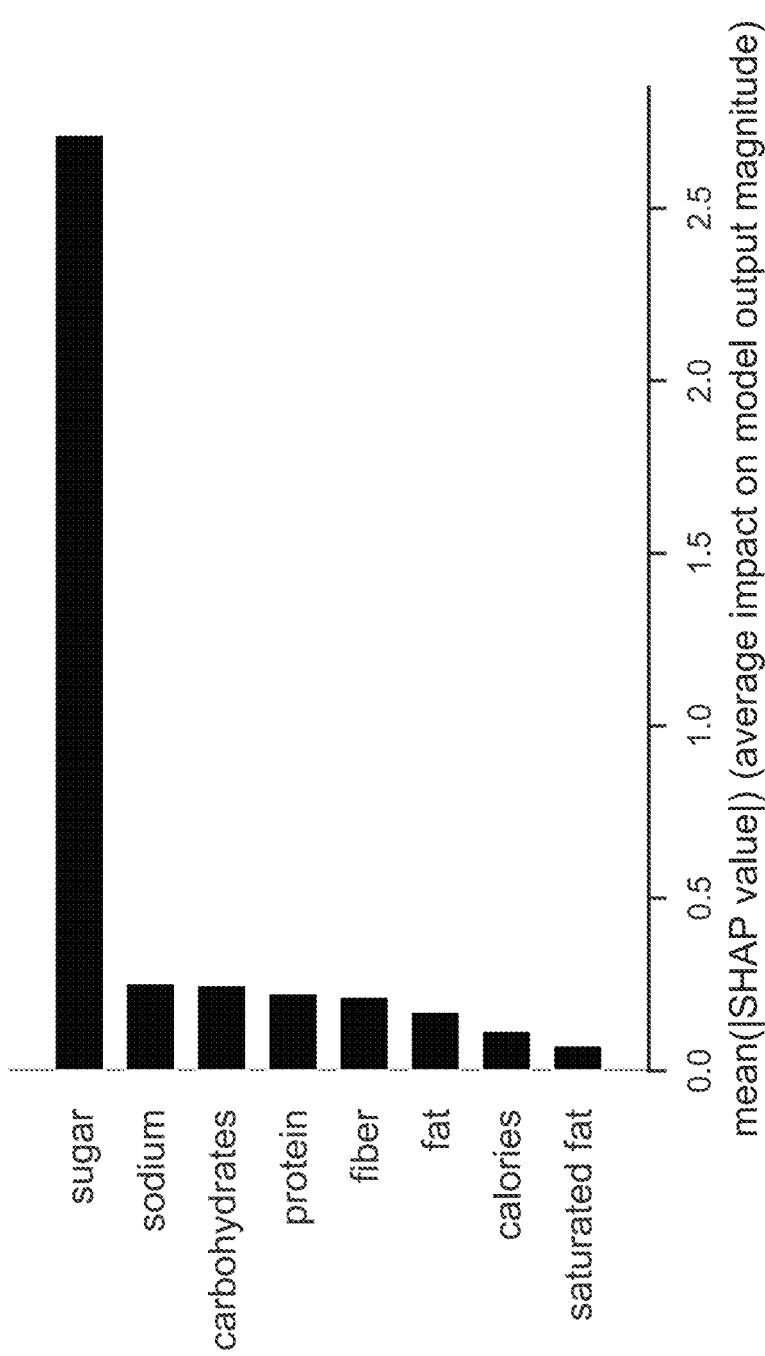
FIG. 13 depicts the mean importance of each feature using the nutrient prediction model engine 117 of the nutrient scoring system 100 in accordance with embodiments of the present disclosure.

FIG. 13 depicts the mean importance of each feature using the nutrient prediction model engine 117 of the nutrient scoring system 100 in accordance with embodiments of the present disclosure. Features of the added sugar estimation are shown on the vertical axis, while the horizontal axis shows the mean absolute SHAP value across predictions, indicating how much the value of each feature contributes to the final prediction. The value of sugar is the most important factor in predicting added sugar.

Figure 14:
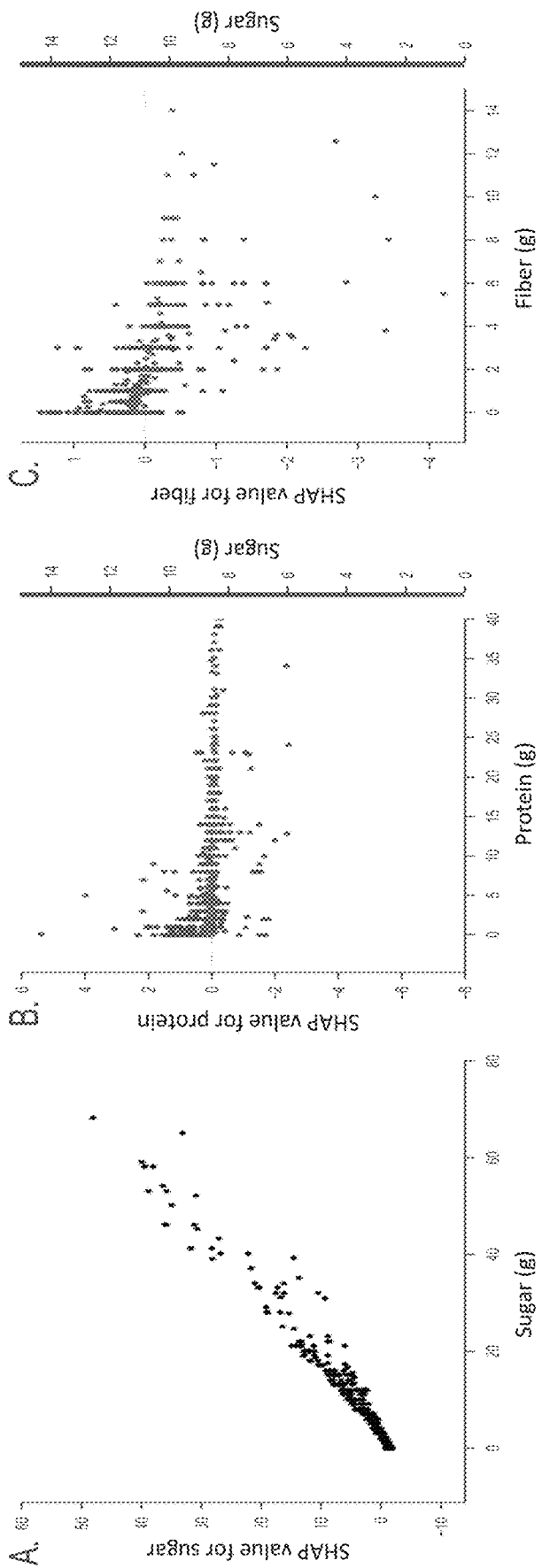
FIG. 14 depicts SHAP dependence plots for select features for the nutrient prediction model engine 117 of the nutrient scoring system 100 in accordance with embodiments of the present disclosure.

FIG. 14 depicts SHAP dependence plots for select features for the nutrient prediction model engine 117 of the nutrient scoring system 100 in accordance with embodiments of the present disclosure. Each dot is a single prediction (row) from the dataset. The value of the feature is displayed on the horizontal axis, while the vertical axis shows how much the value of a feature changed the final model prediction. The bars at the bottom of each chart are histograms showing the distribution of the feature. A. The final model prediction for added sugar depends roughly linearly on sugar. B. Only for high values of sugar does the prediction of added sugar depend on protein. For high values of sugar, lower values of protein indicate higher values of added sugar. C. Low values of fiber indicate higher values of added sugar, especially if the food contains high amounts of sugar.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk(™), TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data score, and other suitable data. In some embodiments, as detailed herein, one or more of the computer-based systems of the present disclosure may be implemented across one or more of various computer platforms such as, but not limited to: (1) FreeBSD, NetBSD, OpenBSD; (2) Linux; (3) Microsoft Windows™; (4) OpenVMS™; (5) OS X (MacOS™); (6) UNIX™; (7) Android; (8) iOS™; (9) Embedded Linux; (10) Tizen™; (11) WebOS™; (12) Adobe AIR™; (13) Binary Runtime Environment for Wireless (BREW™); (14) Cocoa™ (API); (15) Cocoa™ Touch; (16) Java™ Platforms; (17) JavaFX™; (18) QNX™; (19) Mono; (20) Google Blink; (21) Apple WebKit; (22) Mozilla Gecko™; (23) Mozilla XUL; (24) .NET Framework; (25) Silverlight™; (26) Open Web Platform; (27) Oracle Database; (28) Qt™; (29) SAP NetWeaver™; (30) Smartface™; (31) Vexi™; (32) Kubernetes™ and (33) Windows Runtime (WinRT™) or other suitable computer platforms or any combination thereof. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a web site, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

The aforementioned examples are, of course, illustrative and not restrictive.

At least some aspects of the present disclosure will now be described with reference to the following numbered clauses.

Clause 1. A computer-based method comprising:
  receiving, by a processor, from a computing device associated with a user, at least one consumable preference associated with the user;
    wherein the at least one consumable preference identifies the at least one food category, the at least one beverage category or a combination thereof;
  receiving, by the processor, a daily score intake value associated with the user;
  obtaining, by the processor, a content data regarding at least one consumable item;
    wherein the at least one consumable item is at least one food item, at least one beverage item, or a combination thereof;
    wherein the content data comprises a first content data item identifying at least one first amount of at least one first nutrient found in the at least one consumable item;
    wherein the consumable-specific machine learning model comprises a subset of decision trees selected from the decision tree library;
    wherein the automatically generating the consumable-specific machine learning model further comprises:
  determining a plurality of optimal places to generate tree branches for a subset of decision trees selected from the decision tree library;
  automatically applying, by the processor, in real-time, a nutrient prediction machine learning model to the content data regarding the at least one consumable item to predict the at least one second amount of the at least one second nutrient in the at least one consumable item based at least in part on:

i) the first content data item identifying the at least one first amount of the at least one first nutrient found in the at least one consumable item, ii) a second content data item identifying at least one second nutrient having at least one second amount found in the at least one consumable item, and iii) a decision tree library of at least one thousand nutrient decision trees;

determining, by the processor, at least one zero-scored consumable item based, at least in part, on:

i) the daily score intake value associated with the user, ii) the at least one first amount of the at least one first nutrient, iii) the at least one second amount of the at least one second nutrient, and iv) the at least one consumable preference; and instructing, by the processor, the computing device associated with the user to utilize at least one graphical user interface element to identify the at least one zero-scored consumable item on a screen of the computing device.

Clause 2. The method of Clause 1, wherein the nutrient prediction machine learning model comprises a decision tree model having a plurality of branches and a plurality of leaves;

wherein the decision tree model is trained to form each branch of the plurality of branches based at least in part on learned threshold values of nutrient quantities.

Clause 3. The method of Clause 2, wherein the subset of decision trees selected from the decision tree library comprises one hundred decision trees.

Clause 3. The method of Clause 1, further comprising:

instructing, by the processor, the computing device associated with the user to generate a consumable preference questionnaire;

receiving, by the processor, from the computing device associated with the user, answers to the consumable preference questionnaire; and generating, by the processor, the daily score intake value associated with the user based, at least in part on, on the answers to the consumable preference questionnaire.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

The invention claimed is:

1. A computer-based method comprising:

receiving, by the processor, a content data regarding at least one consumable item;

wherein the at least one consumable item is at least one food item, at least one beverage item, or a combination thereof;

wherein the content data comprises a first content data item identifying at least one first amount of at least one first nutrient found in the at least one consumable item;

applying, by the at least one processor, each decision tree in a subset of decision trees to the content data to predict at least one decision tree-specific second amount of at least one second nutrient in the at least one consumable item based at least in part on the first content data item identifying the at least one first amount of the at least one first nutrient found in the at least one consumable item;

wherein each decision tree of the subset of decision trees comprises a plurality of branches and a plurality of leaves;

wherein the subset of decision trees comprises at least one thousand nutrient decision trees; and wherein the decision tree model is trained to form each branch of the plurality of branches based at least in part on learned threshold values of nutrient quantities;

aggregating, by the at least one processor, the at least one decision tree-specific second amount of each decision tree to predict at least one second amount of the at least one second nutrient;

determining, by the processor, the at least one consumable item as at least one zero-scored consumable item, or a score value for the at least one consumable item, based, at least in part, on:

the at least one first amount of the at least one first nutrient, the at least one second amount of the at least one second nutrient; and instructing, by the processor, the computing device associated with the user to utilize at least one graphical user interface element on a screen of the computing device to display at least one of:

the at least one consumable item as the at least one zero-scored consumable item, or the score value for the at least one consumable item.

2. The method of claim 1, further comprising:

receiving, by the at least one processor, at least one known second amount representative of at least one actual amount of the at least one second nutrient in the at least one consumable item;

determining, by the at least one processor, at least one second nutrient prediction error based at least in part on a different between the at least one second amount and the at least one known second amount; and updating, by the at least one processor, the learned threshold values of nutrient quantities of each branch of the plurality of branches of each decision tree in the subset of decision trees based at least in part on the at least one second nutrient prediction error.

3. The method of claim 2, further comprising pruning, by the at least one processor, the subset of decision trees based at least in part on the at least one second nutrient prediction error.

4. The method of claim 1, further comprising:

selecting, by the at least one processor, the subset of decision trees from the decision tree library based at least in part on model parameters;

receiving, by the at least one processor, at least one known second amount representative of at least one actual amount of the at least one second nutrient in the at least one consumable item;

determining, by the at least one processor, at least one second nutrient prediction error based at least in part on a different between the at least one second amount and the at least one known second amount; and updating, by the at least one processor, the model parameters based at least in part on the at least one second nutrient prediction error.

5. The method of claim 1, wherein the nutrient prediction machine learning model comprises a random forest.

6. The method of claim 1, further comprising:
instructing, by the processor, the computing device associated with the user to generate a consumable preference questionnaire;
receiving, by the processor, from the computing device associated with the user, answers to the consumable preference questionnaire; and
generating, by the processor, the daily score intake value associated with the user based, at least in part on, on the answers to the consumable preference questionnaire.

7. The method of claim 1, further comprising utilizing, by the at least one processor, at least one consumable item intake score based at least in part on the at least one first nutrient amount and the at least on second nutrient amount.

8. The method of claim 7, further comprising:
receiving, by the at least one processor, at least one consumption indication indicative of the user having consumed the at least one consumable item; and
updating, by the at least one processor, the daily score intake value by deducting the at least one consumable item intake score in response to the at least one consumption indication.

9. A computer-based system comprising:
at least one processor in communication with at least one non-transitory computer readable medium having software instructions stored thereon, wherein, upon execution of the software instructions, the at least one processor is configured to:
receive a content data regarding at least one consumable item;
wherein the at least one consumable item is at least one food item, at least one beverage item, or a combination thereof;
wherein the content data comprises a first content data item identifying at least one first amount of at least one first nutrient found in the at least one consumable item;
apply each decision tree in a subset of decision trees to the content data to predict at least one decision tree-specific second amount of at least one second nutrient in the at least one consumable item based at least in part on the first content data item identifying the at least one first amount of the at least one first nutrient found in the at least one consumable item;
wherein each decision tree of the subset of decision trees comprises a plurality of branches and a plurality of leaves;
wherein the subset of decision trees comprises at least one thousand nutrient decision trees; and
wherein the decision tree model is trained to form each branch of the plurality of branches based at least in part on learned threshold values of nutrient quantities;
aggregate the at least one decision tree-specific second amount of each decision tree to predict at least one second amount of the at least one second nutrient;
determine the at least one consumable item as at least one zero-scored consumable item, or a score value for the at least one consumable item, based, at least in part, on:
the at least one first amount of the at least one first nutrient,
the at least one second amount of the at least one second nutrient; and
instruct the computing device associated with the user to utilize at least one graphical user interface element on a screen of the computing device to display at least one of:
the at least one consumable item as the at least one zero-scored consumable item, or
the score value for the at least one consumable item.

10. The system of claim 9, wherein, upon execution of the software instructions, the at least one processor is further configured to:
receive at least one known second amount representative of at least one actual amount of the at least one second nutrient in the at least one consumable item;
determine at least one second nutrient prediction error based at least in part on a different between the at least one second amount and the at least one known second amount; and
update the learned threshold values of nutrient quantities of each branch of the plurality of branches of each decision tree in the subset of decision trees based at least in part on the at least one second nutrient prediction error.

11. The system of claim 10, wherein, upon execution of the software instructions, the at least one processor is further configured to prune the subset of decision trees based at least in part on the at least one second nutrient prediction error.

12. The system of claim 9, wherein, upon execution of the software instructions, the at least one processor is further configured to:
select the subset of decision trees from the decision tree library based at least in part on model parameters;
receive at least one known second amount representative of at least one actual amount of the at least one second nutrient in the at least one consumable item;
determine at least one second nutrient prediction error based at least in part on a different between the at least one second amount and the at least one known second amount; and
update the model parameters based at least in part on the at least one second nutrient prediction error.

13. The system of claim 9, wherein the nutrient prediction machine learning model comprises a random forest.

14. The system of claim 9, wherein, upon execution of the software instructions, the at least one processor is further configured to:
instruct the computing device associated with the user to generate a consumable preference questionnaire;
receive from the computing device associated with the user, answers to the consumable preference questionnaire; and
generate the daily score intake value associated with the user based, at least in part on, on the answers to the consumable preference questionnaire.

15. The system of claim 9, wherein, upon execution of the software instructions, the at least one processor is further configured to utilize at least one consumable item intake score based at least in part on the at least one first nutrient amount and the at least on second nutrient amount.

16. The system of claim 15, wherein, upon execution of the software instructions, the at least one processor is further configured to:
receive at least one consumption indication indicative of the user having consumed the at least one consumable item; and update the daily score intake value by deducting the at least one consumable item intake score in response to the at least one consumption indication.

\* \* \* \* \*